US012751681B2

(12) United States Patent
Takahashi et al.

(10) Patent No.: US 12,751,681 B2
(45) Date of Patent: Oct. 6, 2026

(54) X-RAY DIAGNOSTIC APPARATUS, MEDICAL IMAGE PROCESSING APPARATUS, AND MEDICAL IMAGE PROCESSING METHOD

(71) Applicant: CANON MEDICAL SYSTEMS CORPORATION, Otawara (JP)

(72) Inventors: Akihito Takahashi, Nasushiobara (JP); Haruki Iwai, Otawara (JP); Tomoki Fujito, Nasushiobara (JP); Yuki Totsuka, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 417 days.

(21) Appl. No.: 17/993,154

(22) Filed: Nov. 23, 2022

(65) Prior Publication Data

US 2023/0157657 A1 May 25, 2023

(30) Foreign Application Priority Data

Nov. 24, 2021 (JP) ................................ 2021-190452
Nov. 24, 2021 (JP) ................................ 2021-190453

(51) Int. Cl.
*A61B 6/00* (2024.01)
*A61B 6/40* (2024.01)

(52) U.S. Cl.
CPC ................ *A61B 6/482* (2013.01); *A61B 6/40* (2013.01)

(58) Field of Classification Search
CPC ......... A61B 6/482; A61B 6/40; A61B 6/4233; A61B 6/4241; A61B 6/487; A61B 6/5235;
(Continued)

(56) References Cited

U.S. PATENT DOCUMENTS 11,062,489 B2 7/2021 Chen et al.
11,210,779 B2 * 12/2021 Xu ...................... A61B 6/5217
(Continued)

FOREIGN PATENT DOCUMENTS

CN 112862722 * 5/2021 ........... G06K 9/4604
JP 2009-525084 A 7/2009
(Continued)

OTHER PUBLICATIONS

Extended European Search Report Issued Jan. 25, 2023 in European Application 22209420.3, 8 pages.
(Continued)

*Primary Examiner* — Henok Shiferaw
*Assistant Examiner* — Dion J Satcher
(74) *Attorney, Agent, or Firm* — Oblon, McClelland, Maier & Neustadt, L.L.P.

(57) ABSTRACT

According to one embodiment, an X-ray diagnostic apparatus includes processing circuitry. The processing circuitry is configured to acquire a two-dimensional first X-ray image based on X-ray imaging using a first continuous X-ray spectrum, and acquire a two-dimensional second X-ray image based on X-ray imaging using a second continuous X-ray spectrum different from the first continuous X-ray spectrum. Further, the processing circuitry is configured to generate a two-dimensional virtual third X-ray image that simulates an X-ray image using a third continuous X-ray spectrum different from the first continuous X-ray spectrum and the second continuous X-ray spectrum, based on the first X-ray image and the second X-ray image.

19 Claims, 24 Drawing Sheets

(58) Field of Classification Search
CPC . G06T 2207/10116; G06T 2207/20084; G06T 2207/30101; G06T 5/50; G06T 5/60; G06T 5/70; H04N 5/325
USPC .......................................................... 382/128
See application file for complete search history.

(56) References Cited

U.S. PATENT DOCUMENTS

| | | | | |
|---|---|---|---|---|
| 12,056,796 | B2* | 8/2024 | Tao | A61B 6/5211 |
| 2010/0220834 | A1 | 9/2010 | Heismann et al. | |
| 2014/0321603 | A1* | 10/2014 | Taguchi | A61B 6/405 378/5 |
| 2016/0019432 | A1 | 1/2016 | Fredenberg et al. | |
| 2016/0213344 | A1* | 7/2016 | Yi | A61B 6/5282 |
| 2018/0110492 | A1* | 4/2018 | Yeh | A61B 6/032 |
| 2020/0082579 | A1* | 3/2020 | Sekiya | G06T 7/0012 |
| 2020/0146135 | A1 | 5/2020 | Tetsuka et al. | |
| 2020/0196973 | A1* | 6/2020 | Zhou | A61B 6/5258 |
| 2020/0205751 | A1* | 7/2020 | Taguchi | A61B 6/4452 |
| 2020/0281552 | A1* | 9/2020 | McCollough | G16H 50/30 |
| 2021/0004994 | A1* | 1/2021 | Kubo | G01N 23/04 |
| 2021/0007691 | A1 | 1/2021 | Prabhu Verleker et al. | |
| 2021/0267563 | A1 | 9/2021 | Sattarivand et al. | |
| 2022/0309294 | A1* | 9/2022 | Paysan | G06V 10/751 |
| 2022/0383466 | A1 | 12/2022 | Tsukuda et al. | |

FOREIGN PATENT DOCUMENTS

| | | | |
|---|---|---|---|
| JP | 2016-512776 | A | 5/2016 |
| JP | 2020-064720 | A | 4/2020 |
| JP | 2021-010727 | A | 2/2021 |
| JP | 2021-037164 | A | 3/2021 |
| JP | 2021-129717 | A | 9/2021 |

OTHER PUBLICATIONS

Office Action issued Sep. 9, 2025, in corresponding Japanese Patent Application No. 2021-190452, 5 pages.
Office Action issued Sep. 9, 2025, in corresponding Japanese Patent Application No. 2021-190453, with English translation, citing documents 3 and 4 therein, 10 pages.
Office Action issued Feb. 3, 2026, in corresponding Japanese Patent Application No. 2021-190453, with English translation, citing document 5 therein, 9 pages.

* cited by examiner

BONE THICKNESS IMAGE Tbone

SOFT TISSUE THICKNESS IMAGE Ttissue

NORMAL ENERGY VIRTUAL IMAGE iIM

NORMAL ENERGY CAPTURED IMAGE rIM

X-RAY DIAGNOSTIC APPARATUS, MEDICAL IMAGE PROCESSING APPARATUS, AND MEDICAL IMAGE PROCESSING METHOD

CROSS-REFERENCE TO RELATED APPLICATIONS

This application claims the benefit of priority of Japanese Patent Application No. 2021-190452, filed Nov. 24, 2021, and Japanese Patent Application No. 2021-190453, filed Nov. 24, 2021, the entire contents of all of which are incorporated herein by reference.

FIELD

Embodiments described herein relate generally to an X-ray diagnostic apparatus, a medical image processing apparatus, and a medical image processing method.

BACKGROUND

Spectral imaging techniques are known in which X-ray diagnostic apparatus acquires an X-ray image of an object corresponding to each of a plurality of different X-ray energies by varying the energy of X-rays, and discriminates materials in the object, by utilizing the fact that X-ray absorption characteristics that are different between each material.

Spectral imaging technology can perform material discrimination processing to obtain thickness data of each material, as well as energy subtraction processing to suppress specific material components.

In the material discrimination process, a material discrimination image showing thickness distributions of, for example, two specific materials (e.g., bone and soft tissue) can be generated from two X-ray images corresponding to two continuous X-ray spectra (X-ray energies).

In spectral imaging techniques such as material discrimination processing and energy subtraction processing, it is preferable to set a large difference in X-ray energy in order to improve processing accuracy.

For example, when changing the X-ray energy by changing the tube voltage, it is preferable to apply a tube voltage as high as possible (for example, 110-140 kV) for imaging using a high tube voltage, and to apply a tube voltage as low as possible (for example, 40-60 kV) for imaging using a low tube voltage.

On the other hand, in normal clinical practice, an X-ray image acquired by applying an intermediate tube voltage (for example, 70-80 kV) is more suitable for user observation than an X-ray image acquired by applying these extreme tube voltages.

Therefore, though the X-ray images obtained by X-ray imaging in spectral imaging technology can be used for material discrimination processing, and to visualize the difference in the constituent elements of the object, it is difficult to use such X-ray images in usual clinical practice.

As a method of obtaining an image suitable for normal clinical use while increasing the processing accuracy of spectral imaging technology, it is conceivable to separately perform X-ray imaging using intermediate tube voltage in addition to X-ray imaging using extreme tube voltages, but the exposure dose of the object will increase.

DETAILED DESCRIPTION

Hereinbelow, a description will be given of an X-ray diagnostic apparatus, a medical image processing apparatus, and a medical image processing method according to embodiments of the present invention with reference to the drawings.

An X-ray diagnostic apparatus according to an embodiment includes an image acquisition unit and a virtual image generation unit. The image acquisition unit acquires a two-dimensional first X-ray image based on X-ray imaging using a first X-ray energy, and an X-ray image using a second X-ray energy different from the first X-ray energy. The virtual image generation unit generates a two-dimensional virtual third X-ray image that simulates an image using a third X-ray energy different from the first X-ray energy and the second X-ray energy, based on the first X-ray image and the second X-ray image.

An X-ray diagnostic apparatus, a medical image processing apparatus, and a medical image processing method according to an embodiment of the present invention can use spectral imaging technology, and acquire X-ray images that correspond to each of a plurality of continuous X-ray spectra (X-ray energies).

Figure 1:
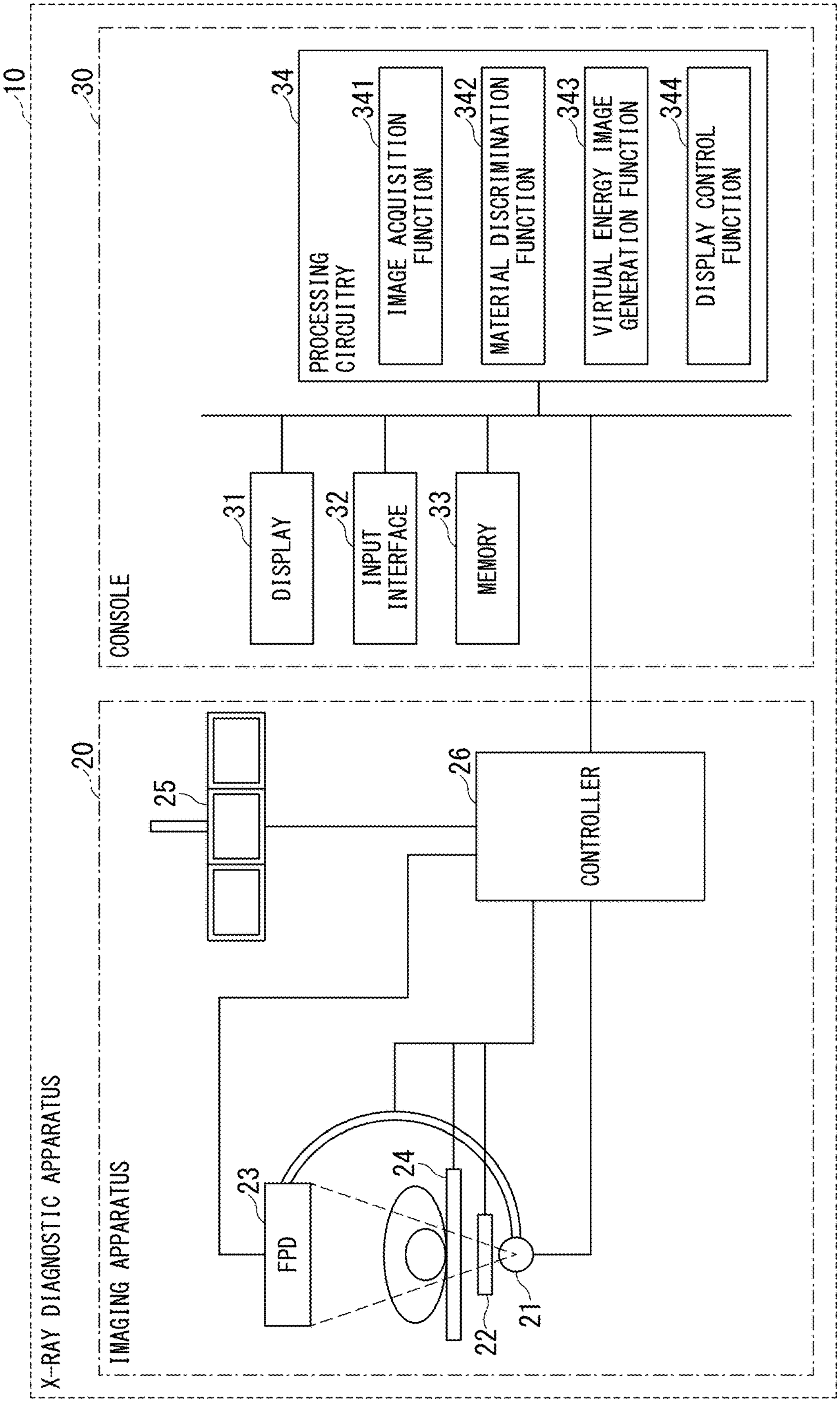
FIG. 1 is a block diagram showing a configuration example of an X-ray diagnostic apparatus including a medical image processing apparatus according to an embodiment.

FIG. 1 is a block diagram showing a configuration example of an X-ray diagnostic apparatus 10 including a medical image processing apparatus according to one embodiment. Note that the X-ray diagnostic apparatus 10 may be any type of X-ray diagnostic apparatuses that can acquire X-ray images corresponding to a plurality of different continuous X-ray spectra (X-ray energies), such as an X-ray TV apparatus, an X-ray angiography apparatus, a general imaging apparatus, and a mammography apparatus.

As shown in FIG. 1, the X-ray diagnostic apparatus 10 has an imaging apparatus 20, and a console 30 as an example of a medical image processing apparatus.

The imaging apparatus 20 is typically installed in an examination room and is configured to generate image data about an object. The console 30, which is an example of a medical image processing apparatus, is installed, for example, in an operation room adjacent to the examination room, and generates and displays an X-ray image based on the image data.

The console 30 may be installed in the examination room where the imaging apparatus 20 is installed, or may be connected to the imaging apparatus 20 via a network and installed in a remote location away from the examination room.

The imaging apparatus 20 has an X-ray tube 21, an X-ray movable diaphragm 22, an FPD 23, a tabletop 24, a display 25, and a controller 26.

The X-ray tube 21 is applied with a high voltage to generate X-rays. The tube voltage applied to the X-ray tube 21 is controlled by the processing circuitry 34 of the console 30.

The X-ray movable diaphragm 22 may be configured of a plurality of lead plates for narrowing the irradiation range of the X-rays generated by the X-ray tube 21, and may form a slit by combining the plurality of lead plates. For example, the X-ray movable diaphragm 22 has two pairs of movable blades, and the irradiation range of X-rays emitted from the X-ray tube 21 is adjusted by opening and closing each pair of movable blades.

FPD 23 is configured of a flat panel detector (FPD) having a plurality of X-ray detection elements (group of imaging elements), and detects the X-rays irradiated to the FPD23. Based on the detected X-rays the FPD 23 outputs image data of X-ray fluoroscopic images and X-ray radiographic images at a predetermined frame. Note that, hereinafter, X-ray fluoroscopic images and X-ray radiographic images are collectively referred to as X-ray images. This image data is given to the console 30.

The FPD 23 has, more specifically, a plurality of X-ray detection elements configured by semiconductor elements that store signal charges corresponding to the amount of incident X-rays. The plurality of X-ray detection elements is arranged in a matrix. As the FPD 23, a CMOS-FPD or the like can be used.

The X-ray tube 21 and the FPD 23 may be arranged to face each other with the object placed on the tabletop 24 interposed therebetween. For example, the X-ray tube 21 and the FPD 23 may be supported at both ends of a support member such as a C-arm so as to face each other across the object as shown in FIG. 1. Alternatively, the X-ray tube 21 and the FPD 23 may be supported by independent support members.

Although FIG. 1 shows an example of an under-tube type of the X-ray diagnostic apparatus 10 in which the C-arm supports the X-ray tube 21 so as to be positioned below the tabletop 24, the X-ray diagnostic apparatus 10 may be an over-tube type that supports the X-ray tube 21 so as to be positioned above the tabletop 24.

In addition, although the single-plane X-ray diagnostic apparatus 10 configured with one C-arm is illustrated in FIG. 1, the X-ray diagnostic apparatus 10 may be a biplane X-ray diagnostic apparatus having two arms.

Also, the C-arm may hold the X-ray tube 21 and the FPD 23 such that the distance between the X-ray tube focus and the X-ray detector (SID: Source Image receptor Distance) can be changed.

A tabletop 24 is provided above the bed, and an object is placed thereon. A high voltage power supply (not shown) is controlled by the processing circuitry 34 of the console 30.

The high voltage power supply includes a high voltage generation unit having a function of generating a high voltage to be applied to the X-ray tube 21, and an X-ray control apparatus for controlling output voltage according to the X-rays emitted by the X-ray tube 21. The high voltage generation unit may be of a transformer type or an inverter type.

The display 25 includes one or more display areas, and displays various information such as images generated by the processing circuitry 34. The display 25 is arranged at a position visible to the user in the examination room, and is configured of a general display output apparatus such as a liquid crystal display or an OLED (Organic Light Emitting Diode) display.

Controller 26 has at least a processor and memory. The controller 26 is controlled by the console 30 according to the program stored in this memory, and comprehensively controls each component of the imaging apparatus 20. For example, the controller 26 is controlled by the console 30 to image an object with a plurality of continuous X-ray spectra, and generate X-ray image data corresponding to each continuous X-ray spectrum (X-ray energy) to provide the generated X-ray image data to the console 30.

On the other hand, console 30 has display 31, input interface 32, memory 33, and processing circuitry 34.

The display 31 is configured of a general display output apparatus such as a liquid crystal display or an OLED (Organic Light Emitting Diode) display, and displays various information such as images generated by the processing circuitry 34 under the control of the processing circuitry 34.

The input interface 32 is implemented by an input device, such as a trackball, a switch, a button, a mouse, a keyboard, a touch pad that performs an input operation by touching an operation surface, a non-contact input interface using an optical sensor, a voice input interface, and the like. The input interface 32 also outputs an input operation signal corresponding to a user's operation to the processing circuitry 34. Further, the input interface 32 includes an exposure switch that controls the on/off of X-ray radiation.

The memory 33 has a configuration including a processor-readable recording medium such as a magnetic or optical recording medium or a semiconductor memory. Some or all of the programs and data in the storage medium of the memory 33 may be downloaded via an electronic network, or provided to the memory 33 via a portable storage medium such as an optical disc.

The processing circuitry 34 implements a function of comprehensively controlling the X-ray diagnostic apparatus 10. In particular, the processing circuitry 34 reads out and executes the image processing program stored in the memory 33, thereby improving the processing accuracy of the spectral imaging technology, while performing processing for obtaining an image suitable for normal clinical use based on the X-ray imaging acquired by the spectral imaging technology.

The processor of the processing circuitry 34 implements an image acquisition function 341, a material discrimination function 342, a virtual energy image generation function 343, and a display control function 344, as shown in FIG. 1. Each of these functions is stored in the memory 33 in the form of a program. Some of the functions 341-344 of the processing circuitry 34 may be implemented by an external processor connected to the console 30 via a network such that data can be transmitted and received.

The image acquisition function 341 acquires a two-dimensional first X-ray image based on X-ray imaging using a first continuous X-ray spectrum (hereinafter referred to as first X-ray energy), and acquires a two-dimensional second X-ray image based on X-ray imaging using a second continuous X-ray spectrum (hereinafter referred to as second X-ray energy) that is different from the first X-ray energy. The image acquisition function 341 is an example of an image acquisition unit.

A change in the X-ray energy, that is, a change in the wavelength distribution of the continuous X-ray spectrum can be realized by switching the tube voltage, changing the beam filter, or the like.

The first X-ray image and the second X-ray image may be acquired in real time from the imaging apparatus 20 by controlling the imaging apparatus 20 to perform X-ray imaging. Alternatively, the first X-ray image and the second X-ray image may be obtained in post-processing from the X-ray diagnostic apparatus 10 or from an image server connected to the X-ray diagnostic apparatus 10 via a network after the examination by the X-ray diagnostic apparatus 10 is completed.

The image server is, for example, a server for long-term storage of images provided in a PACS (Picture Archiving and Communication System), which stores X-ray images such as fluoroscopic images and DSA (digital subtraction angiography) images.

In the following description, the first X-ray image will be referred to as the high energy captured image IH corresponding to the high tube voltage, and the second X-ray image will be referred to as the low energy captured image IL corresponding to the low tube voltage.

Based on the first X-ray image and the second X-ray image, the material discrimination function 342, through material discrimination processing, generates a first material discrimination image showing the thickness distribution of the first material, and a second material discrimination image showing the thickness distribution of the second material.

In the following description, an example will be described in which the first material discrimination image is a bone thickness image Tbone obtained by discriminating bones by material discrimination processing based on the first X-ray image and the second X-ray image, and the second material discrimination image is a soft tissue thickness image Ttissue obtained by discriminating the soft tissue by material discrimination processing based on the first X-ray image and the second X-ray image. The material discrimination function 342 is an example of a discrimination unit.

Based on the first X-ray image and the second X-ray image, the virtual energy image generation function 343 generates a two-dimensional virtual third X-ray image that simulates an X-ray image using a third continuous X-ray spectrum (hereinafter referred to as the third X-ray energy) different from the first X-ray energy and the second X-ray energy. The virtual energy image generation function 343 is an example of a virtual image generation unit.

The virtual energy image generation function 343 simulates spectral projection corresponding to the third x-ray energy by virtually adjusting at least one of the tube voltage and beam filter.

In the following description, an example is shown in which the tube voltage corresponding to the third X-ray energy (normal energy) is an intermediate tube voltage between the high tube voltage corresponding to the first X-ray energy (high energy) and the low tube voltage corresponding to the second X-ray energy (low energy). Note that, in the following description, the virtual third X-ray image is referred to as normal energy virtual image ImaginaryIM (iIM).

The display control function 344 causes the display 25 or the display 31 to display the virtual third X-ray image in parallel with at least one of the first material discrimination image and the second material discrimination image. Alternatively, the display control function 344 may cause the display 25 or the display 31 to display the virtual third X-ray image superimposed on at least one of the first material discrimination image and the second material discrimination image, or superimposed on an image based on at least one of the first material discrimination image and the second material discrimination image. The display control function 344 is an example of a display control unit.

First Embodiment

First, the first embodiment of the X-ray diagnostic apparatus 10, medical image processing apparatus, and medical image processing method will be described with reference to FIGS. 2 to 4.

Figure 2:
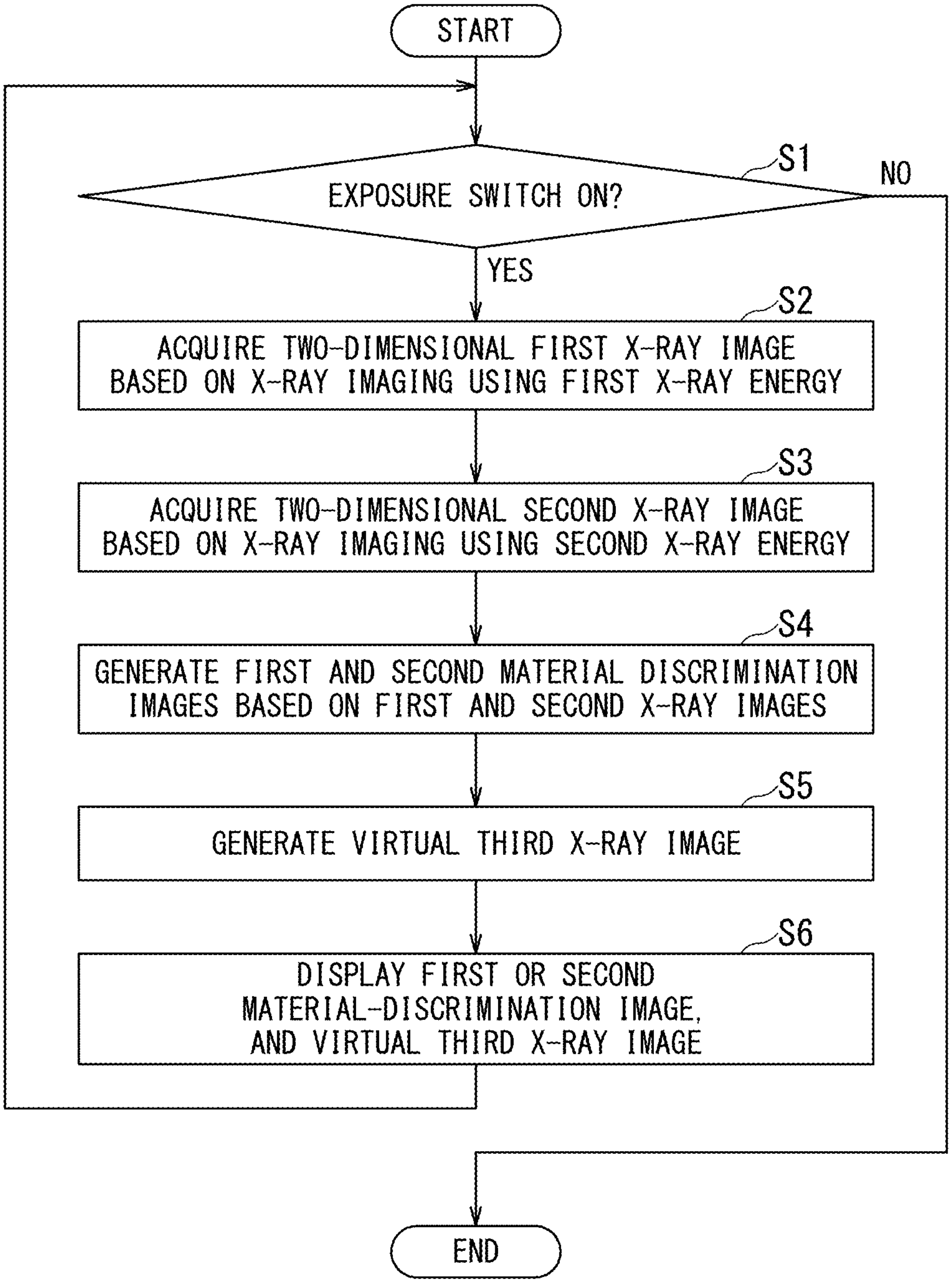
FIG. 2 is a flowchart showing an example of a procedure for obtaining an image suitable for normal/usual clinical use based on X-ray imaging acquired by spectral imaging technology while increasing the processing accuracy of spectral imaging technology by the processor of the processing circuit shown in FIG. 1.

FIG. 2 shows a flowchart showing an example of a procedure for obtaining an image suitable for normal/usual clinical use based on X-ray imaging acquired by spectral imaging technology, while increasing the processing accuracy of spectral imaging technology by the processor of processing circuitry 34 shown in FIG. 1. In FIG. 2, numerals attached to S indicate respective steps of the flow chart.

Figure 3:
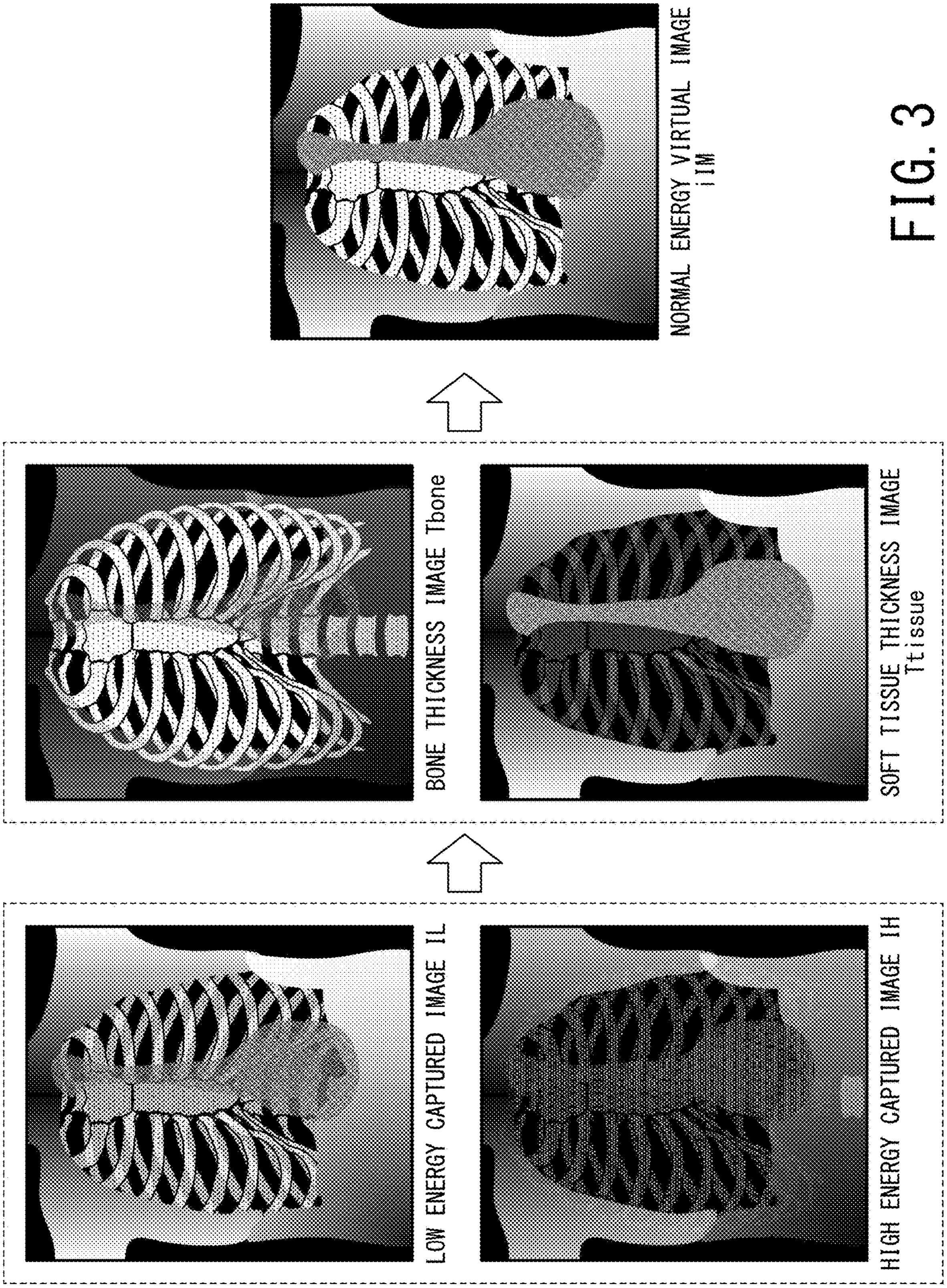
FIG. 3 is an explanatory view showing each image example when the normal energy virtual image iIM is generated based on the high energy captured image IH and the low energy captured image IL.

FIG. 3 is an explanatory diagram showing image examples when the normal energy virtual image iIM is generated based on the high energy captured image IH and the low energy captured image IL.

Figure 4:
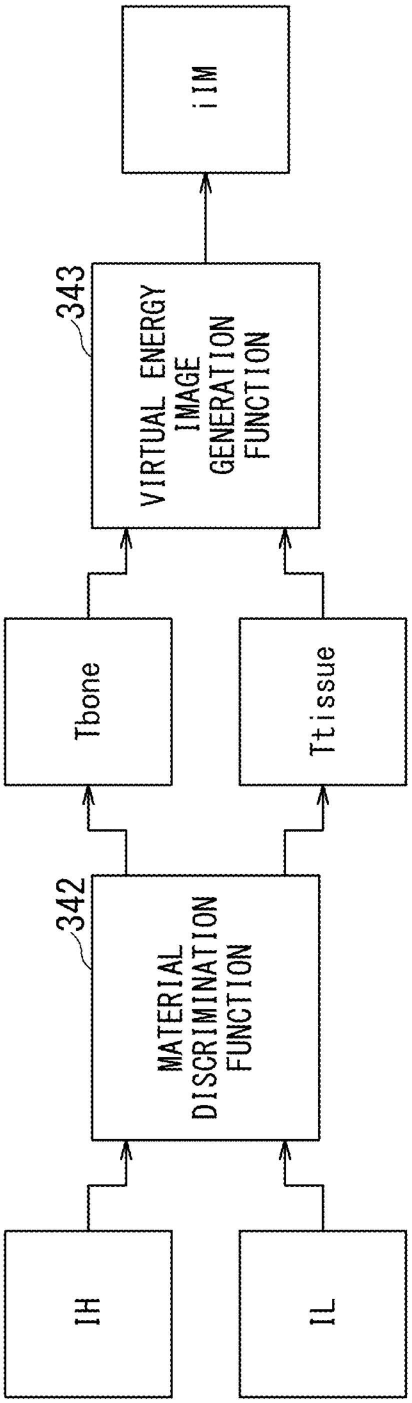
FIG. 4 is a diagram showing an example of a data flow when generating a normal energy virtual image iIM according to the first embodiment.

FIG. 4 is a diagram showing an example of a data flow when generating a normal energy virtual image iIM according to the first embodiment.

The procedure shown in FIG. 2 is applicable to X-ray imaging by the X-ray diagnostic apparatus 10, and is also applicable to continuous X-ray imaging having a predetermined frame-rate, such as fluoroscopic imaging performed by the X-ray angiography apparatus, DA (Digital Angiography) imaging, or DSA (Digital Subtraction Angiography) imaging.

First, in step S1, the image acquisition function 341 determines whether or not the exposure switch of the input interface 32 has been turned on. When the exposure switch has not yet been turned on (NO in step S1), the series of procedures ends.

On the other hand, when the exposure switch has been turned on (YES in step S1), the image acquisition function 341 acquires a two-dimensional high energy captured image IH based on X-ray imaging using the first X-ray energy (step S2), and acquires a two-dimensional low energy captured image IL based on X-ray imaging using a second X-ray energy (step S3). The order of steps S2 and S3 may be reversed.

X-ray imaging using the first X-ray energy and X-ray imaging using the second X-ray energy are performed by switching tube voltages, for example. In this case, the imaging corresponding to the high tube voltage and the imaging corresponding to the low tube voltage may be performed with different X-ray pulses, or may be performed by switching the tube voltage while the X-ray tube 21 is emitting one X-ray pulse. In the latter case, the FPD 23 capable of non-destructive read out may be used, and non-destructive read out from the FPD 23 may be performed according to the switch of the tube voltage.

Next, in step S4, the material discrimination function 342 generates a bone thickness image Tbone and a soft tissue thickness image Ttissue by material discrimination processing based on the high energy captured image IH and the low energy captured image IL (see FIGS. 3 and 4).

In the procedure shown in FIGS. 2 to 4, the material discrimination function 342 calculates such thickness dbone of bone (bone and contrast-enhanced blood vessel, etc.) and soft tissue thickness dsoft that satisfies the following simultaneous equations (1) and (2), for each pixel of the high energy captured image IH and the low energy captured image IL.

$$I^{(high)}/I_0^{(high)} = \frac{\int_0^{high\ kVp} N^{(high)}(E)\exp(-\mu_{bone}(E)d_{bone} - \mu_{soft}(E)d_{soft})EdE}{\int_0^{high\ kVp} N^{(high)}(E)EdE} \quad (1)$$

$$I^{(low)}/I_0^{(low)} = \frac{\int_0^{low\ kVp} N^{(low)}(E)\exp(-\mu_{bone}(E)d_{bone} - \mu_{soft}(E)d_{soft})EdE}{\int_0^{low\ kVp} N^{(low)}(E)EdE} \quad (2)$$

wherein, $$I_0^{(high)} = \int_0^{high\ kVp} N^{(high)}(E)EdE \quad (3)$$

$$I_0^{(low)} = \int_0^{low\ kVp} N^{(low)}(E)EdE \quad (4)$$

In equations (1) to (4), $N^{(high)}$ (E) represents the spectrum of the first X-ray energy, $N^{(low)}$ (E) represents the spectrum of the second X-ray energy, $\mu_{bone}$ (E) represents the X-ray absorption coefficient of bones, etc., and $\mu_{soft}$(E) represents the absorption coefficient of soft tissue. Note that $N^{(high)}$(E), $N^{(low)}$(E), $\mu_{bone}$(E), and, $\mu_{soft}$ (E) are previously stored in the memory 33 as known values.

Then, the material discrimination function 342 generates a bone thickness image Tbone by assigning a luminance value corresponding to the thickness dbone of the bone obtained for each pixel, and generates a soft tissue thickness image Ttissue by assigning a luminance value corresponding to the thickness dsoft of the soft tissue obtained for each pixel.

Next, in step S5, the virtual energy image generation function 343 generates a normal energy virtual image iIM, which is a two-dimensional virtual X-ray image, based on the high energy captured image IH and the low energy captured image IL.

In the procedure shown in FIGS. 2 to 4, the virtual energy image generation function 343 generates a virtual normal energy virtual image iIM, by performing virtual projection processing using a virtual X-ray energy spectrum for each pixel of the bone thickness image Tbone and the soft tissue thickness image Ttissue.

Specifically, the virtual energy image generation function 343 substitutes the bone thickness dbone and the soft tissue thickness dsoft obtained in step S4 into the following equation (5). Then, the virtual energy image generation function 343 generates a normal energy virtual image iIM, by simulating the projection for each pixel using the spectrum $N^{(middle)}$ (E) of virtual third X-ray energy (for example, normal energy suitable for normal clinical use), (see FIGS. 3 and 4).

$$I^{(middle)} = \int_0^{middle\ kVp} (N^{(middle)}(E)\exp(-\mu_{bone}(E)d_{bone} - \mu_{soft}(E)d_{soft})EdE \quad (5)$$

The virtual third X-ray energy spectrum $N^{(middle)}$ (E) may be simulated by virtually setting the tube voltage, or by virtually switching the beam filter, or by virtually adjusting both the tube voltage and the beam filter.

In addition, the virtual energy image generation function 343 uses Equation (5) to generate a second normal energy virtual image based on the virtual fourth X-ray energy spectrum $N^{(middle2)}$ (E). For example, when a virtual third X-ray energy corresponds to a tube voltage of 80 kV, a virtual fourth X-ray energy may correspond to a slightly smaller tube voltage, such as 70 kV.

Next, in step S6, the display control function 344 displays the normal energy virtual image iIM in parallel with, and/or, superimposed on at least one of the bone thickness image Tbone and the soft tissue thickness image Ttissue on the display 25 or the display 31, and then, the process returns to step S1.

Here, in the superimposed display, the normal energy virtual image iIM may be used as the main image, and the bone thickness image Tbone and/or the soft tissue thickness image Ttissue may be superimposed as subordinate images, or vice versa.

Alternatively, in superimposed display, the bone thickness image Tbone and/or the soft tissue thickness image Ttissue can be replaced by an image obtained by extracting the contour of the bone thickness image Tbone and/or the soft tissue thickness image Ttissue.

Furthermore, at least one of the images to be superimposed may be displayed in a chromatic color so that the superimposed images can be readily distinguished and recognized.

In addition to or instead of displaying at least one of the bone thickness image Tbone and the soft tissue thickness image Ttissue, which are the results of material discrimination, a normal energy virtual image iIMafter image processing (for example, enhancement of a specific spatial frequency component) based on the material discrimination result, may be displayed.

Using the above procedure, it is possible to obtain an image suitable for normal clinical use based on the X-ray image acquired by the spectral imaging technique while improving the processing accuracy of the spectral imaging technique.

In addition, the image acquisition function 341 and the virtual energy image generation function 343 may sequentially repeat combination of the acquisition of the high energy captured image IH, the acquisition of the low energy captured image IL and generation of the normal energy virtual image iIM, on the condition that the user continues the exposure instruction, for example, via the exposure switch.

The X-ray diagnostic apparatus 10 can obtain a third X-ray image (for example, normal energy virtual image iIM) based on a plurality of X-ray images obtained by X-ray imaging in spectral imaging technology.

Therefore, simply by performing X-ray imaging using high X-ray energies in the spectral imaging technique, it is possible not only to generate material discrimination images such as a bone thickness image Tbone and a soft tissue thickness image Ttissue but also to virtually generate and display an image suitable for normal clinical practice, without specially performing X-ray imaging for generating an image suitable for normal clinical practice, thereby preventing increased exposure dose of the object.

First Modification of First Embodiment

Figure 5:
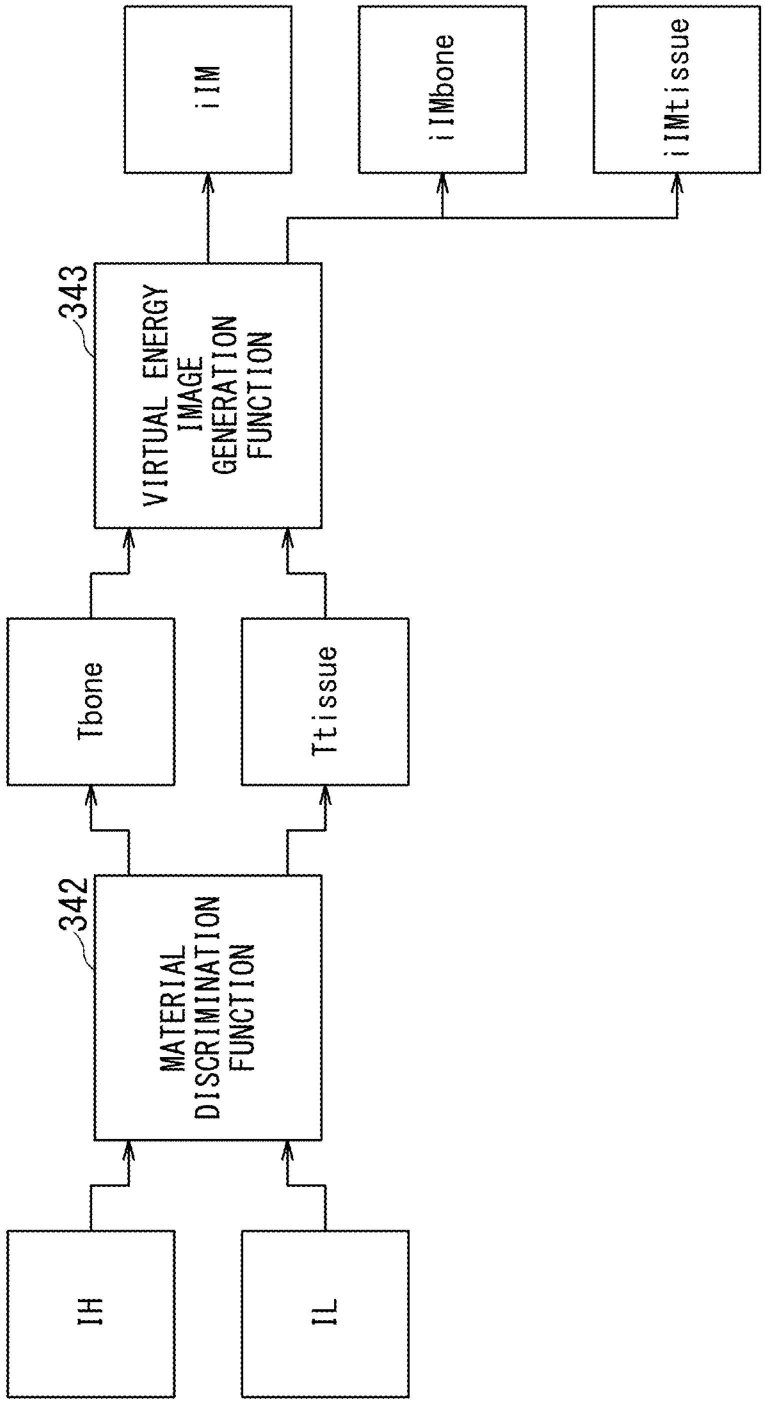
FIG. 5 is a diagram showing an example of a data flow when generating a virtual first material discrimination image (normal energy virtual bone image iIMbone) simulating X-ray imaging using a third X-ray energy of a first material and a second material, and a virtual second material discrimination image (normal energy virtual soft tissue image iIMtissue).

FIG. 5 shows an example of data flow in which a virtual first material discrimination image (normal energy virtual bone image ilMbone) and a virtual second material discrimination image (normal energy virtual soft tissue image ilMtissue), which respectively simulate X-ray images using third X-ray energies of the first material and the second material, are further generated.

The bone thickness image Tbone and the soft tissue thickness image Ttissue are images showing the thickness distribution of materials. For this reason, the bone thickness image Tbone and the soft tissue thickness image Ttissue have contrasts different from those of a normal X-ray image, which may be unfamiliar to the user and make intuitive observation difficult.

Therefore, the virtual energy image generation function 343 may substitute only one of the thickness dbone of the bone and the thickness dsoft of the soft tissue into the equation (5), simulate the projection for each pixel using the virtual X-ray energy spectrum $N^{(middle)}$ (E) used in normal clinical practice, and generate a normal energy virtual bone image ilMbone and a normal energy virtual soft tissue image ilMtissue (see FIG. 5).

In this case, the display control function 344 may use the normal energy virtual bone image ilMbone and the normal energy virtual soft tissue image ilMtissue instead of the bone thickness image Tbone and the soft tissue thickness image Ttissue.

By displaying the normal energy virtual bone image ilMbone and the normal energy virtual soft tissue image ilMtissue, instead of the bone thickness image Tbone and the soft tissue thickness image Ttissue, the user can observe an image with familiar contrast, resulting in that a more accurate diagnosis can be made.

In addition, there are cases where it is desired to make the discriminative image of the intended material (e.g., bone) more visible, or to decrease the visibility of the discriminative image of the unintended material (e.g., soft tissue).

Accordingly, when performing the calculation according to formula (5), in the former case, the thickness dbone of the bone is uniformly multiplied by a numerical value greater than 1, while in the latter case, dsoft is uniformly multiplied by a numerical value smaller than 1, which enables to generate a discriminative image having the desired visibility.

A similar effect can be available by, for example, using a different spectrum N(middle) (E) for each material in the calculation of Equation (2).

Second Modification of First Embodiment

The virtual energy image generation function 343 may generate a normal energy virtual image iIM from the high energy captured image IH and the low energy captured image IL, using a trained model constructed by machine learning. In this case, deep learning using multi-layered neural networks such as CNN (convolutional neural network) and convolutional deep belief network (CDBN) may be used as machine learning.

Hereinafter, an example in which the virtual energy image generation function 343 uses a trained model constructed by deep learning will be described. Note that in this case, step S4 in FIG. 2 may be omitted. When step S4 in FIG. 2 is omitted, only the normal energy virtual image iIM is displayed in step S6 in FIG. 2.

Figure 6:
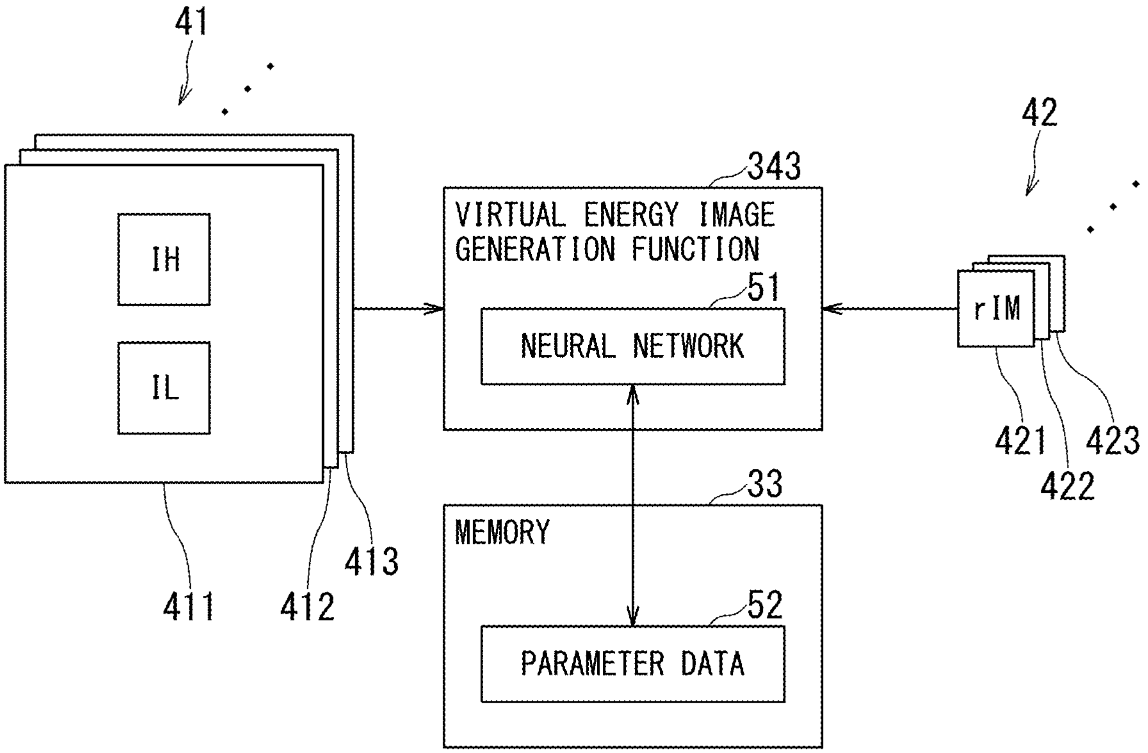
FIG. 6 is an explanatory diagram showing an example of a data flow during learning of the virtual energy image generation function according to the first embodiment.

FIG. 6 is an explanatory diagram showing an example of data flow during learning of the virtual energy image generation function 343 according to the first embodiment. The virtual energy image generation function 343 sequentially updates the parameter data 52 by performing deep learning using a large number of training datasets.

Each dataset of a plurality of training datasets consists of training data 41 and teaching data 42. The training data 41 consists of datasets 411, 412, 413 . . . of high energy captured images IH and low energy captured images IL. The teaching data 42 consists of actual third X-ray images (normal energy actual images) rIM421, 422, 423, which are acquired by actually performing X-ray imaging using the third X-ray energy.

Each of the actual third X-ray images (normal energy actual images) rIM 421, 422, 423 . . . is acquired under the same imaging conditions as each of the sets 411, 412, 413, of the high energy captured image IH and the low energy captured image IL, except for the X-ray energy.

The virtual energy image generation function 343 updates the parameter data 52 so that the result of processing the training data 41 by the neural network 51 approaches the teaching data 42 each time a training data set is given, which is called learning.

In general, when the change rate of the parameter data 52 converges within a threshold value, it is determined that the learning has ended. Hereinafter, the parameter data 52 after learning is particularly referred to as trained parameter data 52*t*. The neural network 51 and the trained parameter data 52*t* constitute the trained model 50.

Figure 7:
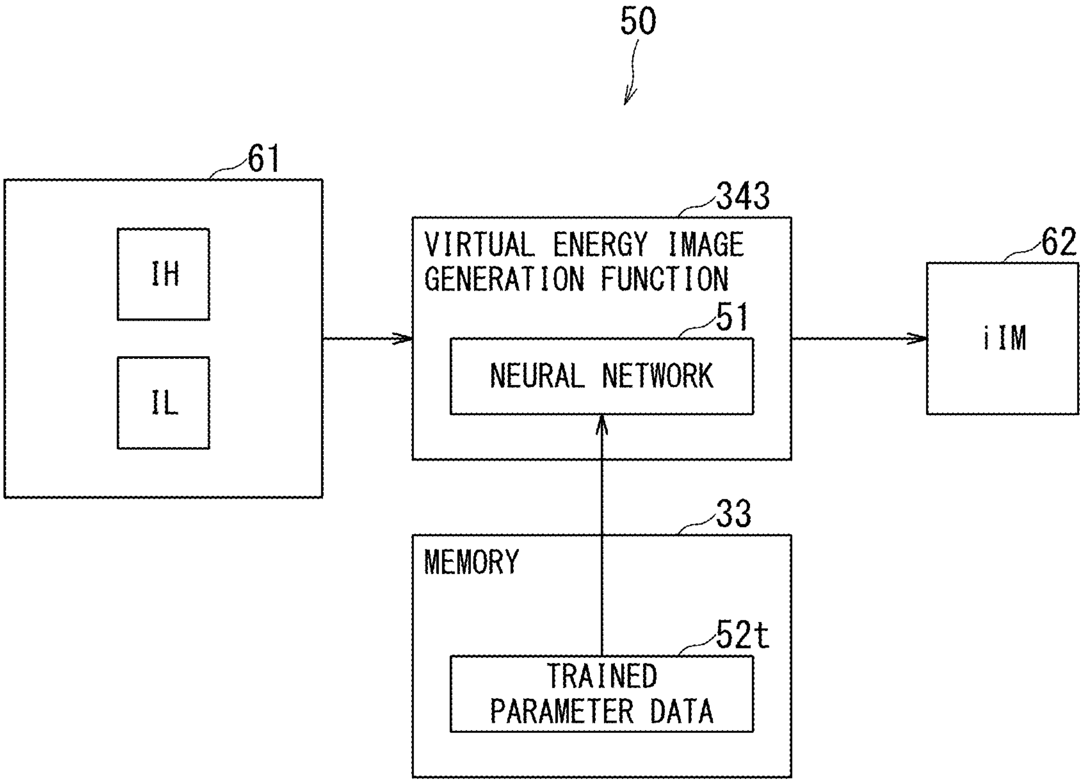
FIG. 7 is an explanatory diagram showing an example of a data flow during operation of the virtual energy image generation function according to the first embodiment.

FIG. 7 is an explanatory diagram showing an example of data flow during operation of the virtual energy image generation function 343 according to the first embodiment.

During operation, the virtual energy image generation function 343 receives a set 61 of the high energy captured image IH and the low energy captured image IL, and uses the trained model 50 to generate a normal energy virtual image iIM62. A trained model 50 is configured of a neural network 51 and trained parameter data 52*t*. Various methods are well known for this type of learning and constructing a trained model.

The neural network 51 is stored in the memory 33 in the form of a program. The trained parameter data 52*t* may be stored in the memory 33, or may be stored in a storage medium connected to the processing circuitry 34 via a network.

When the trained model 50 (the neural network 51 and the trained parameter data 52*t*) is stored in the memory 33, the virtual energy image generation function 343, which is implemented by the processor of the processing circuitry 34, reads out the trained model 50 from the memory 33 and executes it to generate the normal energy virtual image iIM from the high energy captured image IH and the low energy captured image IL.

Note that the trained model 50 may be constructed by an integrated circuit such as an ASIC (Application Specific Integrated Circuit) or an FPGA (Field Programmable Gate Array).

Second Embodiment

Figure 8:
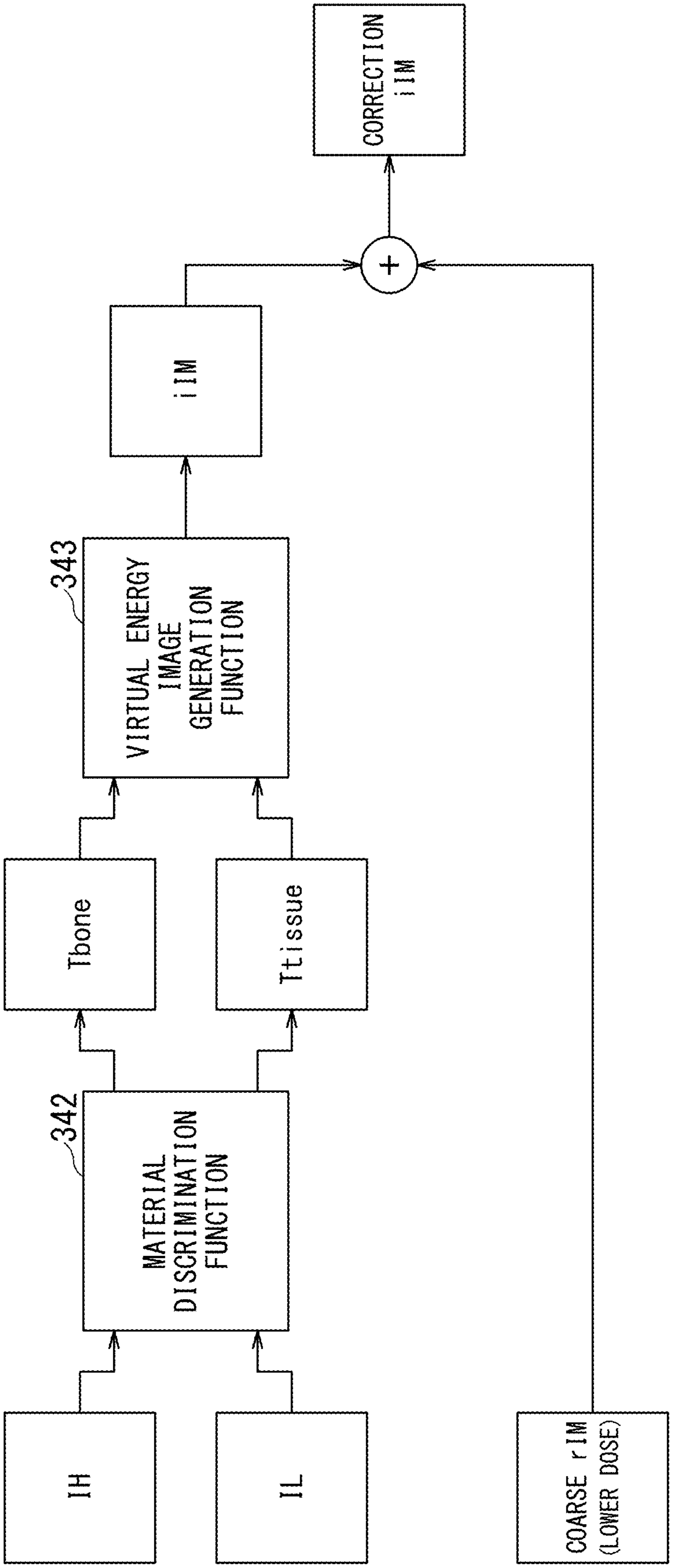
FIG. 8 is a diagram showing an example of a data flow when generating a correction iIM obtained by correcting a normal energy virtual image iIM.

FIG. 8 is a diagram illustrating one example of a data flow when a correction iIM obtained by correcting the normal energy virtual image iIM is generated.

The normal energy virtual image iIM generated by the method according to the first embodiment may be corrected with use of an actual third X-ray image rIM acquired by actually performing X-ray imaging with use of the third X-ray energy.

In this case, it is preferred that the actual X-ray imaging using the third X-ray energy be performed at a dose lower than the dose in normal X-ray imaging so as to reduce the exposure dose on the object. In this case, the acquired third X-ray image becomes an image (roughness rIM) that is rougher than a normal image. However, a virtual image (correction iIM) that has significantly higher image quality than the normal energy virtual image iIM can be acquired by correcting the normal energy virtual image iIM by processing using the roughness rIM acquired by the actual X-ray imaging such as addition of the roughness rIM and the normal energy virtual image iIM.

When the abovementioned approach is used, the dose in the actual X-ray imaging for acquiring the third X-ray image rIM can be made smaller than the dose in a case where an X-ray image having the same SN ratio as the correction iIM is acquired by X-ray imaging. In other words, with use of the abovementioned approach, the dose can be reduced as compared to a method where X-ray imaging for acquiring an X-ray image suitable for normal clinical use is separately performed.

In the description above, the normal energy virtual image iIM is described as an image subjected to correction processing, and the actual third X-ray image rIM is described to be used as an image for correction processing. However, the normal energy virtual image iIM and the actual third X-ray image rIM are images similar to each other besides the noise amount and the like. Therefore, the distinction between the image subjected to correction processing and the image for correction processing is merely for convenience. The essence lies in the feature where an image that has higher image quality than the normal energy virtual image iIM is acquired by using the actual third X-ray image rIM in addition to the normal energy virtual image iIM. Thus, even when the actual third X-ray image rIM is subjected to correction processing or when the normal energy virtual image iIM and the actual third X-ray image rIM are handled equally without a master-servant relationship in terms of data processing, the acquired high quality image is deemed as the correction iIM or a "corrected virtual third X-ray image".

Modification of Second Embodiment

The correction iIM may be generated from the high energy captured image IH, the low energy captured image IL, and the roughness rIM with use of a trained model constructed by machine learning.

Figure 9:
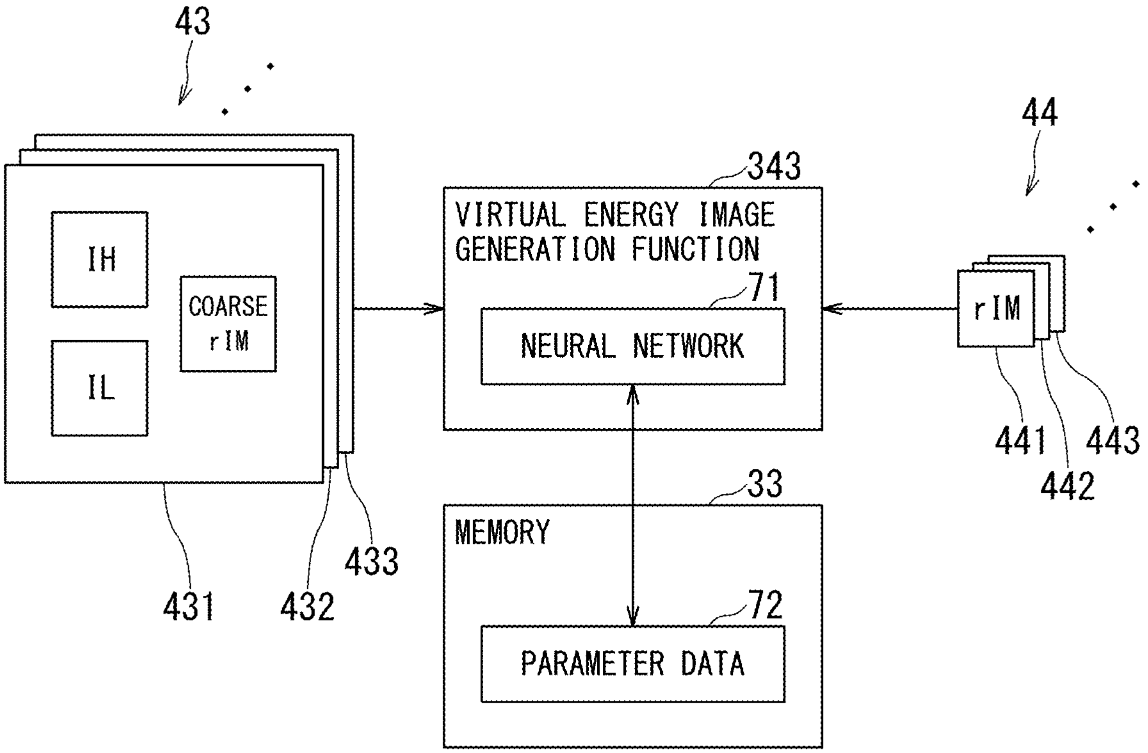
FIG. 9 is an explanatory diagram showing an example of a data flow during learning of a virtual energy image generation function according to a modification of the second embodiment.

FIG. 9 is an explanatory diagram illustrating one example of a data flow at the time of learning of the virtual energy image generation function 343 according to a modification of the second embodiment. The virtual energy image generation function 343 according to the modification of the second embodiment sequentially updates parameter data 72 by performing deep learning with use of a large number of training datasets.

Each training data set of the large number of training datasets consists of training data 43 and teaching data 44. The training data 43 consists of datasets 431, 432, 433, . . . of the high energy captured image IH, the low energy captured image IL, and the roughness rIM. The teaching data 44 consists of actual third X-ray images rIM 441, 442, 443, . . . acquired by actually performing X-ray imaging with use of the third X-ray energy. The actual third X-ray images rIM 441, 442, 443, . . . are high-image-quality detailed images acquired by performing X-ray imaging with use of the third X-ray energy at a dose equal to or more than that of normal X-ray imaging.

The roughness rIM of the training data 43 may be generated by adding noise to each of the actual third X-ray images rIM 441, 442, 443, . . . without actually performing X-ray imaging.

Each time a training dataset is given, the virtual energy image generation function 343 acquires trained parameter data 72*t* by updating the parameter data 72 such that a result obtained by processing the training data 43 by the neural network 71 approaches the training data 44. The neural network 71 and the trained parameter data 72*t* configure a trained model 70.

Figure 10:
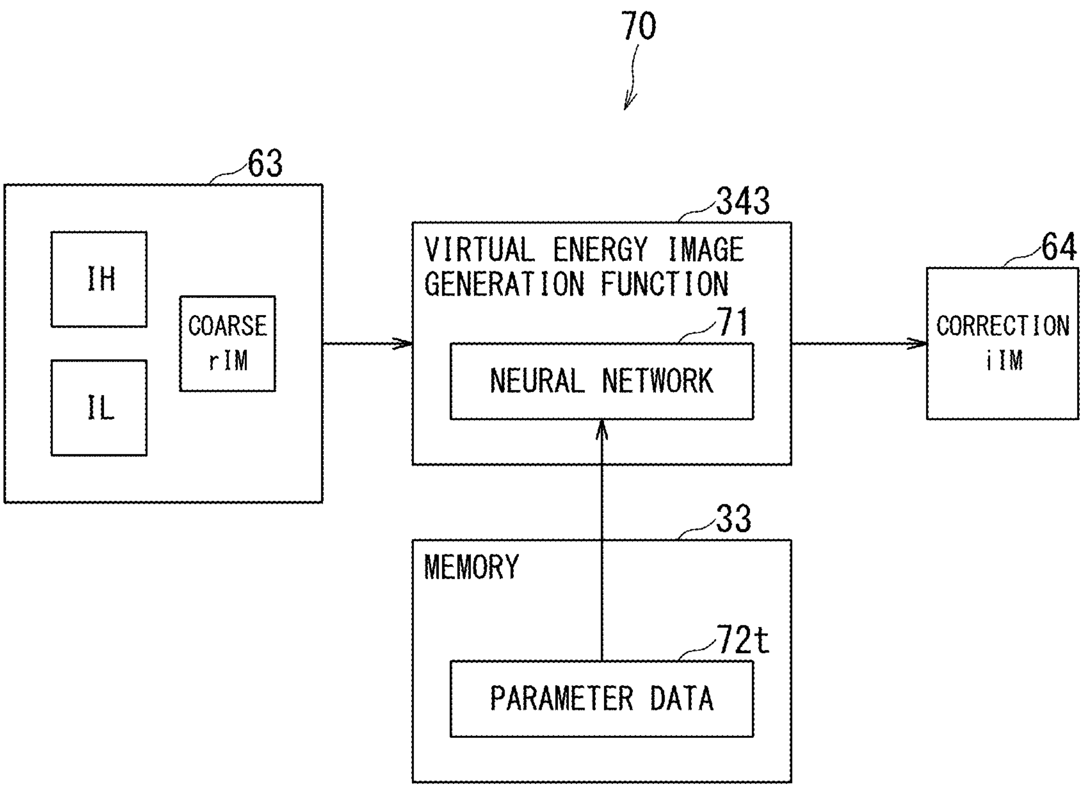
FIG. 10 is an explanatory diagram showing an example of data flow during operation of a virtual energy image generation function according to a modification of the second embodiment.

FIG. 10 is an explanatory diagram illustrating one example of a data flow at the time of operation of the virtual energy image generation function 343 according to the modification of the second embodiment.

In the modification of the second embodiment, at the time of operation, the virtual energy image generation function 343 only needs an input of a set 63 of the high energy captured image IH, the low energy captured image IL, and the roughness rIM and generate a corrected normal energy virtual image iIM (correction iIM) 64 with use of the trained model 70.

Third Embodiment

The X-ray diagnostic apparatus 10, a medical image processing apparatus, and a medical image processing method described in a third embodiment are different from those in the first embodiment and the second embodiment in that contrast-enhanced blood vessels are discriminated.

Figure 11A:
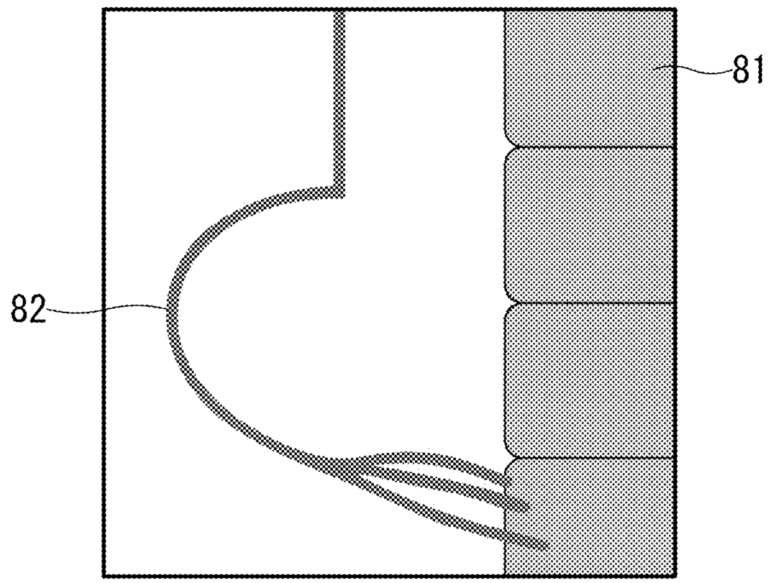
FIG. 11A is a diagram showing an example of a bone thickness image Tbone.
Figure 11B:
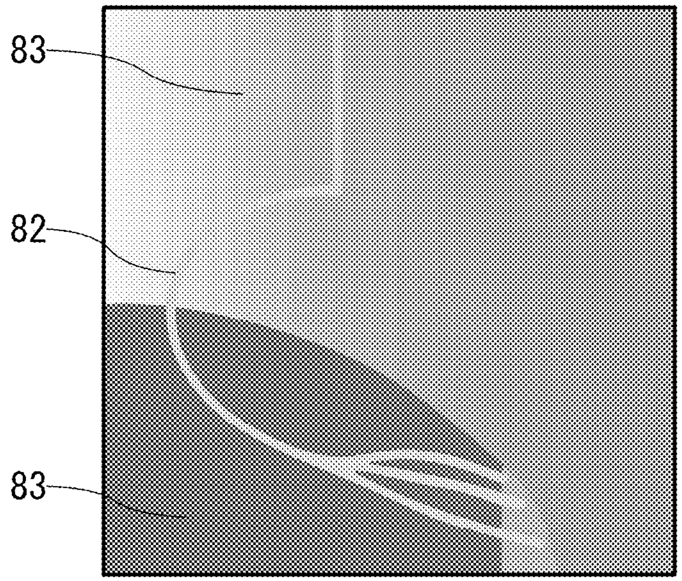
FIG. 11B is a diagram showing an example of a soft tissue thickness image Ttissue.
Figure 12A:
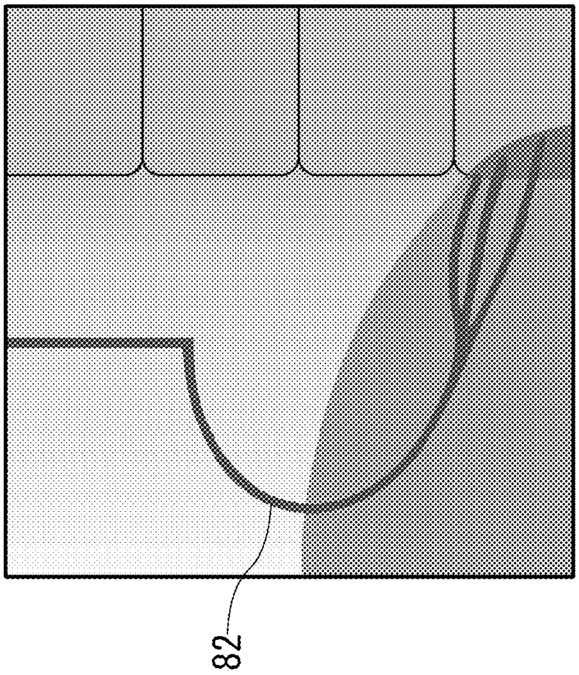
FIG. 12A is a diagram showing an example of a normal energy virtual image iIM.
Figure 12B:
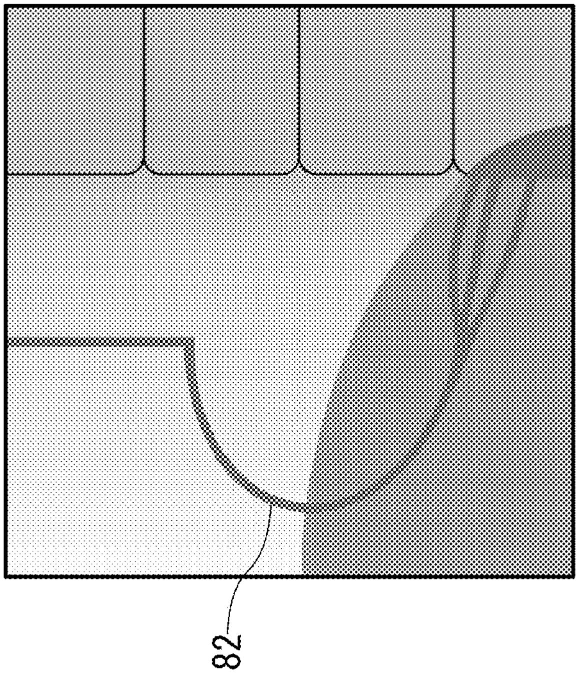
FIG. 12B is a diagram showing an example of a normal energy captured image rIM.
Figure 13:
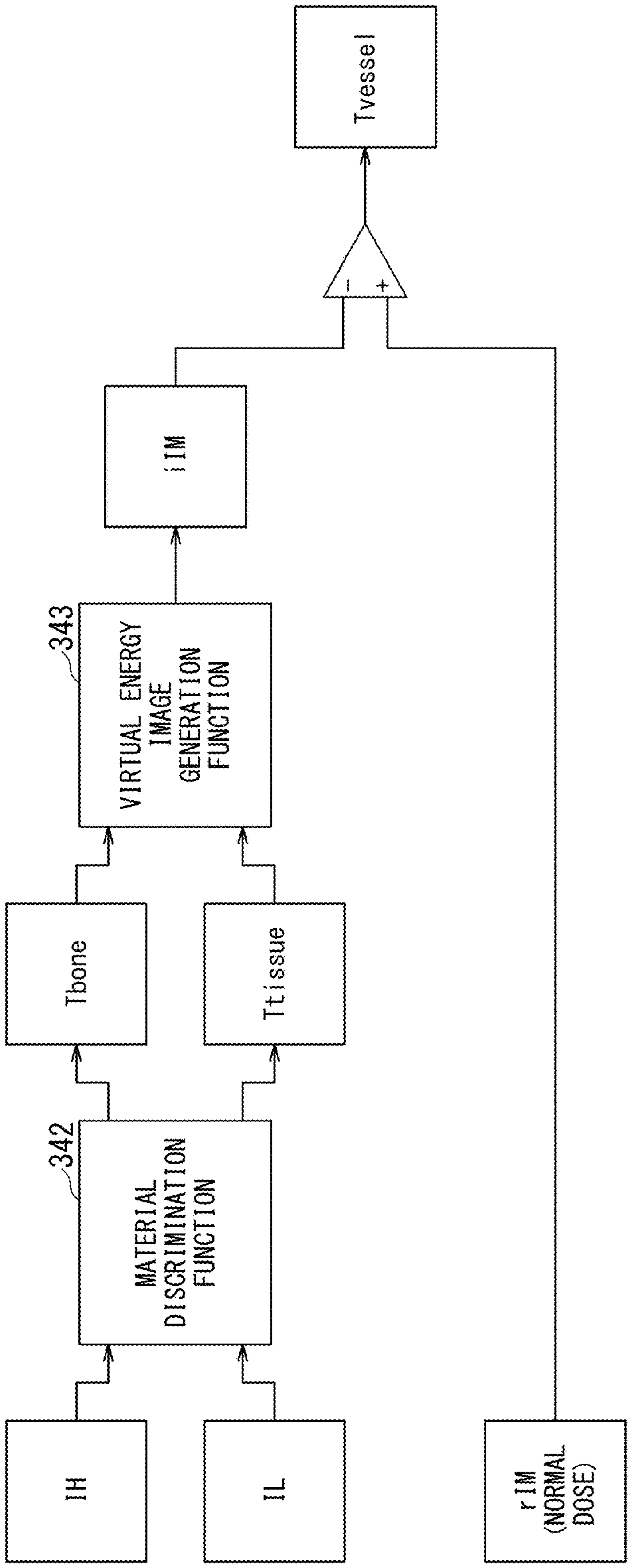
FIG. 13 is a diagram showing an example of a data flow when generating a contrast-enhanced blood vessel thickness image Tvessel.

FIG. 11A is a view showing one example of the bone thickness image Tbone, and FIG. 11B is a view showing one example of the soft-tissue thickness image Ttissue. FIG. 12A is a view showing one example of the normal energy virtual image iIM, and FIG. 12B is a view showing one example of the normal energy captured image rIM. FIG. 13 is a diagram illustrating one example of a data flow when a contrast-enhanced blood vessel thickness image Tvessel is generated.

Now, consider a case where bones, contrast-enhanced blood vessels, and soft tissues are included in a field of view of the X-ray imaging. The X-ray absorption coefficient of the contrast agent for performing contrast imaging of a blood vessel is high and is close to that for performing contrast imaging of a bone. The material discrimination function 342 regards the absorption coefficient of the contrast-enhanced blood vessel 82 as an absorption coefficient $d_{bone}$ (E) of a bone 81 and obtains the thickness dbono of the bone and the like with use of equations (1) and (2). Therefore, in the bone thickness image Tbone generated by the material discrimination function 342 on the basis of the thickness donne, the thickness distribution of the contrast-enhanced blood vessel 82 is visualized as a material having a thickness converted into that of the bone 81 together with the thickness distribution of the bone 81 (see FIG. 11A).

In the soft-tissue thickness image Ttissue generated by the material discrimination function 342, the thickness distribution of a soft tissue 83 is visualized. At this time, in the soft-tissue thickness image Ttissue, a pixel in which the soft tissue 83 and the contrast-enhanced blood vessel 82 are projected in an overlapping manner has a luminance value obtained by causing the thickness of the soft tissue 83 to be thinner by the amount of the thickness of the contrast-enhanced blood vessel 82 (see FIG. 11B).

However, the absorption coefficients of the bone 81 and the contrast-enhanced blood vessel 82 are not actually the same. Thus, the density difference between the contrast-enhanced blood vessel 82 and other components differs between the normal energy virtual image iIM (see FIG. 12A), which is virtually generated from the bone thickness image Tbone and the soft-tissue thickness image Ttissue by the virtual energy image generation function 343, and the normal energy actual image rIM (see FIG. 12B) generated by actual X-ray imaging using normal/usual X-ray energy.

Therefore, the material discrimination function 342 according to the third embodiment can generate the contrast-enhanced blood vessel thickness image Ttissue, which is a contrast-enhanced blood vessel discrimination image obtained by discriminating the contrast-enhanced blood vessel 82 by comparing and taking the difference between the normal energy virtual image iIM and the actual normal energy actual image rIM (see FIG. 13), for example.

Fourth Embodiment

Figure 14:
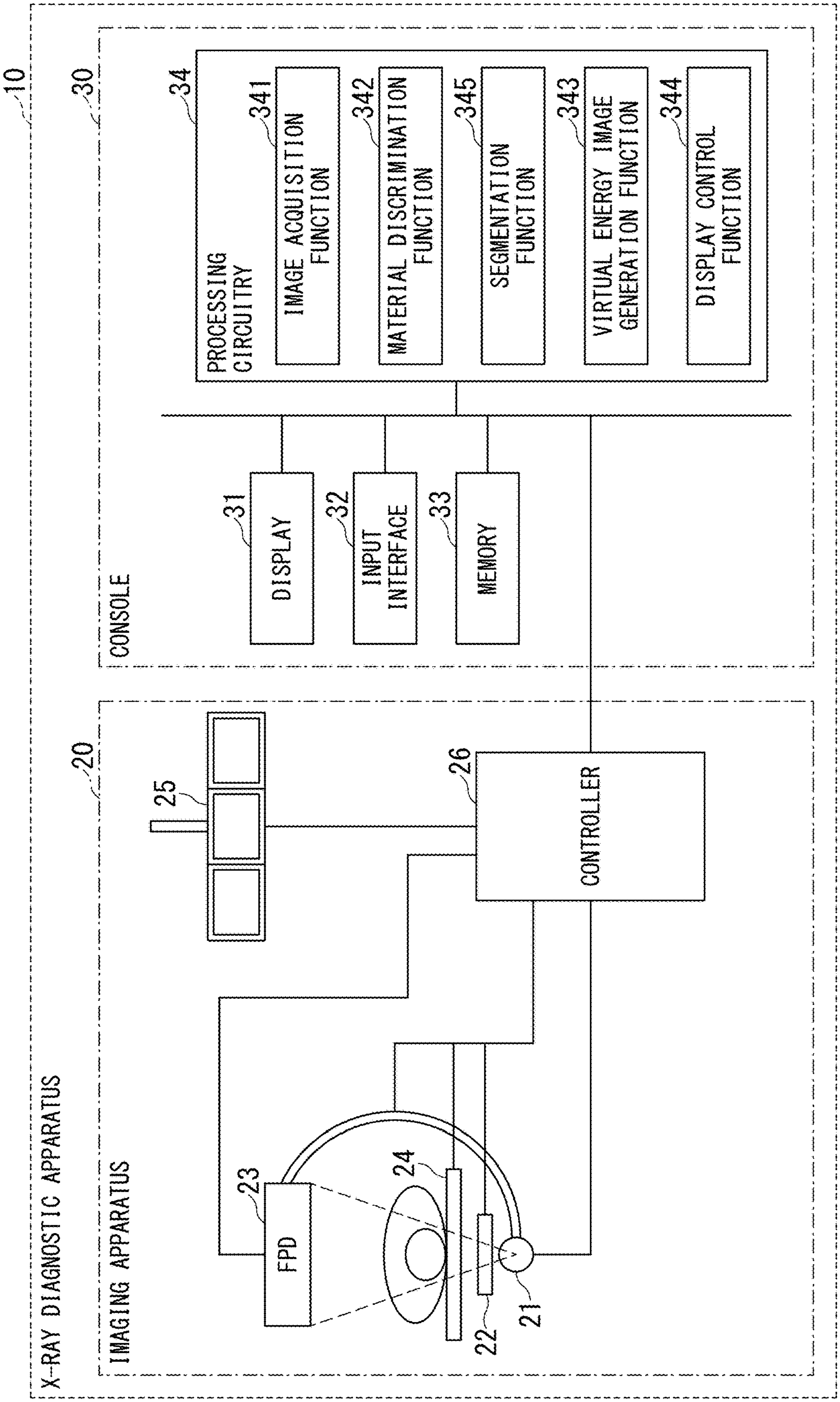
FIG. 14 is a block diagram showing a configuration example of an X-ray diagnostic apparatus 10 including a medical image processing apparatus according to a fourth embodiment.

FIG. 14 is a block diagram illustrating one configuration example of the X-ray diagnostic apparatus 10 including the medical image processing apparatus according to the fourth embodiment.

The X-ray diagnostic apparatus 10 described in the fourth embodiment is different from the X-ray diagnostic apparatus 10 described in the first embodiment in that the processing circuitry 34 segments a target (object to be observed) at a high accuracy on the basis of X-ray images respectively corresponding to a plurality of X-ray energies. Regarding other configurations and effects are substantially from the same as the X-ray diagnostic apparatus 10 illustrated in FIG. 1, and thus, the same configurations are denoted by the same reference characters, and description thereof is omitted.

The target includes bones, contrast-enhanced blood vessels, soft tissues, and the like included in the X-ray image.

As illustrated in FIG. 14, a processor of the processing circuitry 34 further realizes a segmentation function 345 in addition to the image acquisition function 341, the material discrimination function 342, the virtual energy image generation function 343, and the display control function 344. Each of those functions is stored in the memory 33 in a form of a program. Some of the functions 341 to 345 of the processing circuitry 34 may be realized by an external processor connected to the console 30 over a network which enables data transmission and reception.

The image acquisition function 341 according to the fourth embodiment acquires a two-dimensional first X-ray image including a target based on X-ray imaging using a first X-ray energy and acquires a two-dimensional second X-ray image including the target based on X-ray imaging using a second X-ray energy different from the first X-ray energy.

The segmentation function 345 performs the segmentation of the target on the basis of the first X-ray image and the second X-ray image. The segmentation function 345 is one example of a segmentation unit.

The display control function 344 according to the fourth embodiment displays the image of the segmented target on the display 25 or the display 31 in parallel with or being superimposed on a virtual third X-ray image. The display control function 344 may display the image of the segmented target on the display 25 or the display 31 in a manner of being superimposed on the first X-ray image or the second X-ray image.

Figure 15:
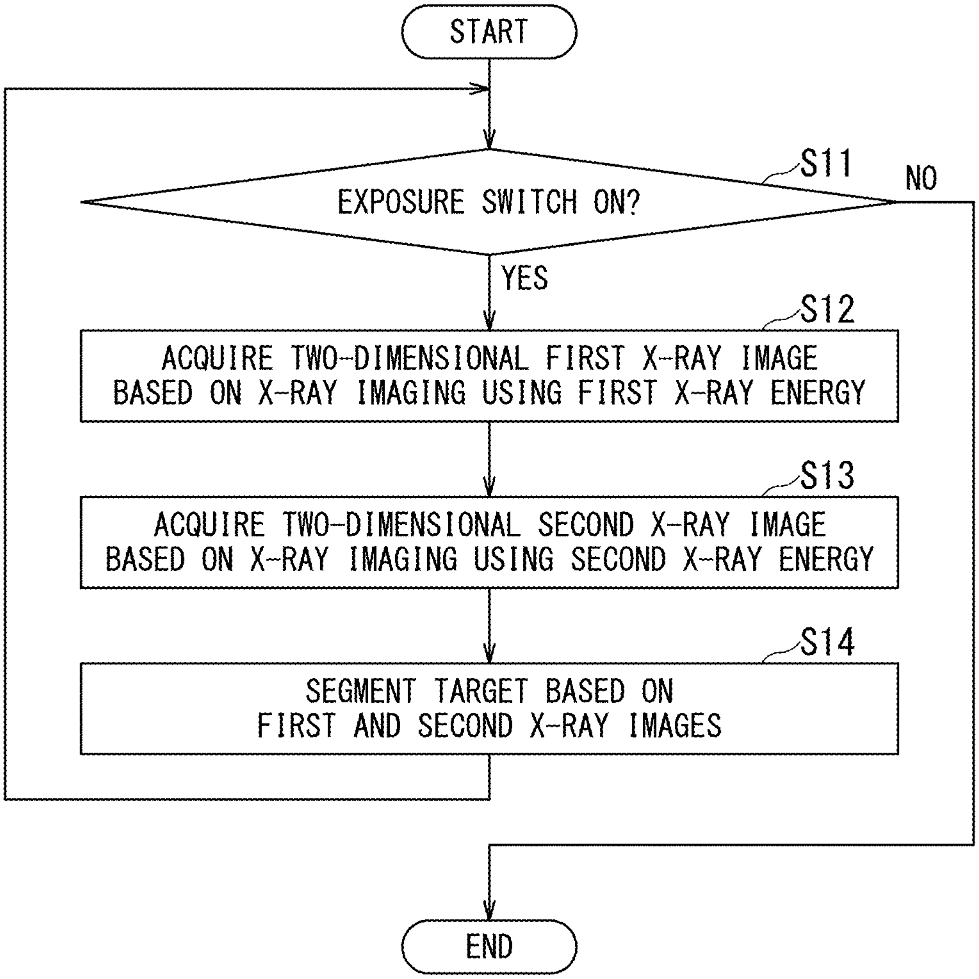
FIG. 15 is a flow chart showing an example of a schematic procedure for highly accurate target segmentation based on corresponding X-ray images of a plurality of X-ray energies by the processor of the processing circuitry shown in FIG. 14.

FIG. 15 is a flowchart illustrating one example of schematic procedures when the segmentation of the target is performed at a high accuracy on the basis of X-ray images respectively corresponding to a plurality of X-ray energies by the processor of the processing circuitry 34 illustrated in FIG. 14. In FIG. 14, numerals attached to S indicate steps of the flowchart.

First, in Step S11, the image acquisition function 341 determines whether the radiation exposure switch of the input interface 32 is turned on. When the radiation exposure switch is not turned on (NO in Step S11), the procedure ends. When the exposure switch has been turned on (YES in Step S11), the image acquisition function 341 acquires the two-dimensional high energy captured image IH including the target (for example, the contrast-enhanced blood vessel) based on X-ray imaging using the first X-ray energy (Step S12) and acquires the two-dimensional low energy captured image IL including the target (for example, the contrast-enhanced blood vessel) based on X-ray imaging using the second X-ray energy (Step S13). The order of Step S2 and Step S3 may be reversed.

Next, in Step S14, the segmentation function 345 segments the target (for example, the contrast-enhanced blood vessel) on the basis of the high energy captured image IH and the low energy captured image IL.

By the procedures above, the segmentation of the target is performed on the basis of the X-ray images respectively corresponding to the plurality of X-ray energies. By using the X-ray images respectively corresponding to the plurality of X-ray energies, the target can be segmented at a higher accuracy as compared to segmentation based on one X-ray image corresponding to one X-ray energy.

A segmentation method of the target based on the X-ray images respectively corresponding to the plurality of X-ray energies is described in detail below. Further, an example of a case where the target is a contrast-enhanced blood vessel will be described below.

Figure 16:
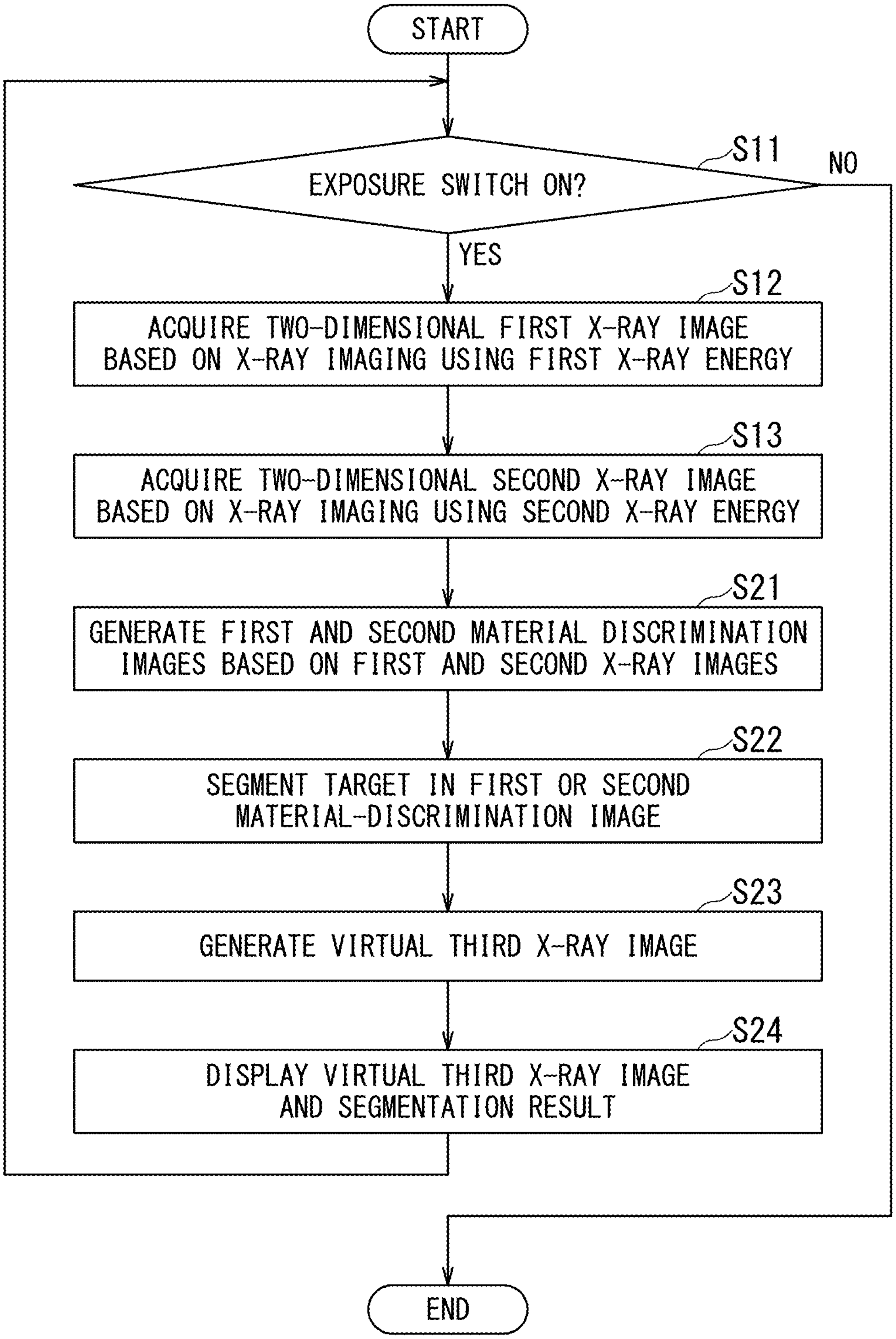
FIG. 16 is a flowchart showing an example of a segmentation procedure according to the fourth embodiment.

FIG. 16 is a flowchart illustrating one example of segmentation procedures according to the fourth embodiment. In FIG. 16, numerals attached to S indicate steps of the flowchart. Steps equivalent to those in FIG. 2 are denoted by the same numerals, and overlapping description thereof is omitted.

Figure 17A:
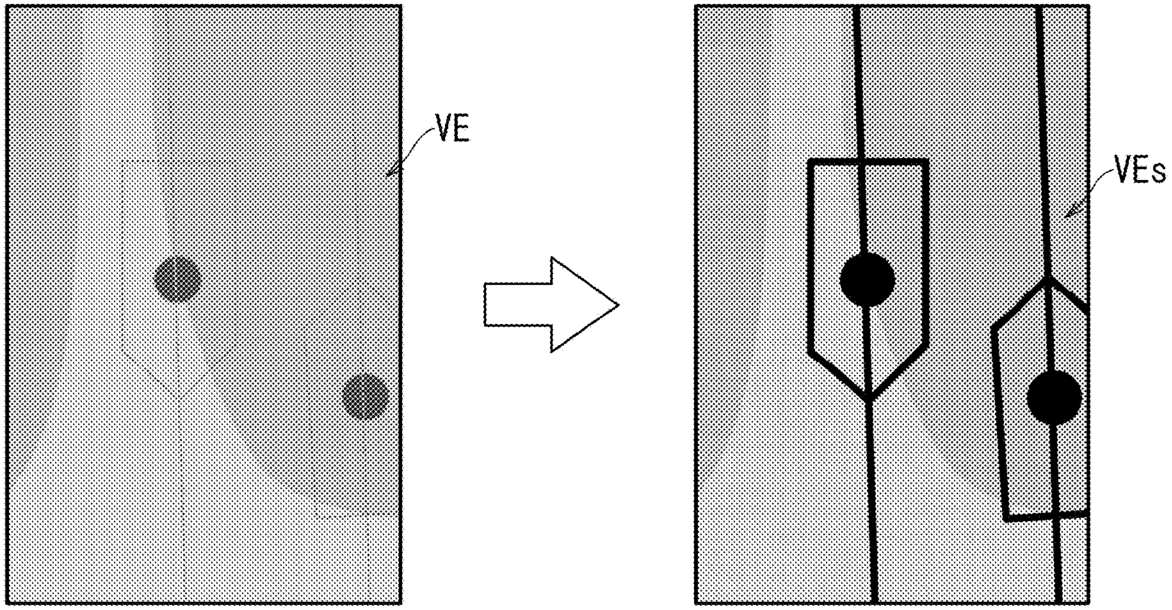
FIG. 17A is an explanatory diagram showing an example of a bone thickness image Tbone and a bone thickness image Tbone_seg obtained by segmenting a contrast-enhanced blood vessel.
Figure 17B:
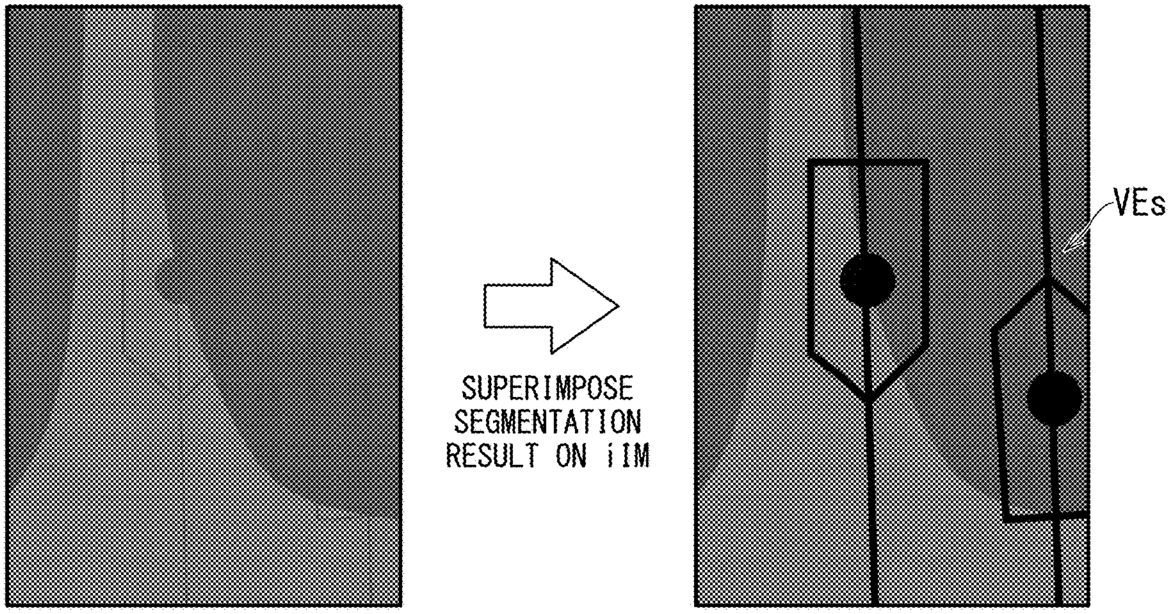
FIG. 17B is an explanatory diagram showing an example of a superimposed image obtained by superimposing a normal energy virtual image iIM and contrast-enhanced blood vessels VEs segmented on the virtual image iIM.

FIG. 17A is an explanatory diagram showing one example of the bone thickness image Tbone and a bone thickness image Tbone_seg obtained by segmenting the contrast-enhanced blood vessel (hereinafter referred to as vessel segmented image Tbone_seg or blood-vessel segmentation-completed image Tbone_seg), and FIG. 17B is an explanatory diagram showing one example of the normal energy virtual image iIM and a superimposed image obtained by superimposing a segmented contrast-enhanced blood vessels VEs on the virtual image iIM.

Figure 18:
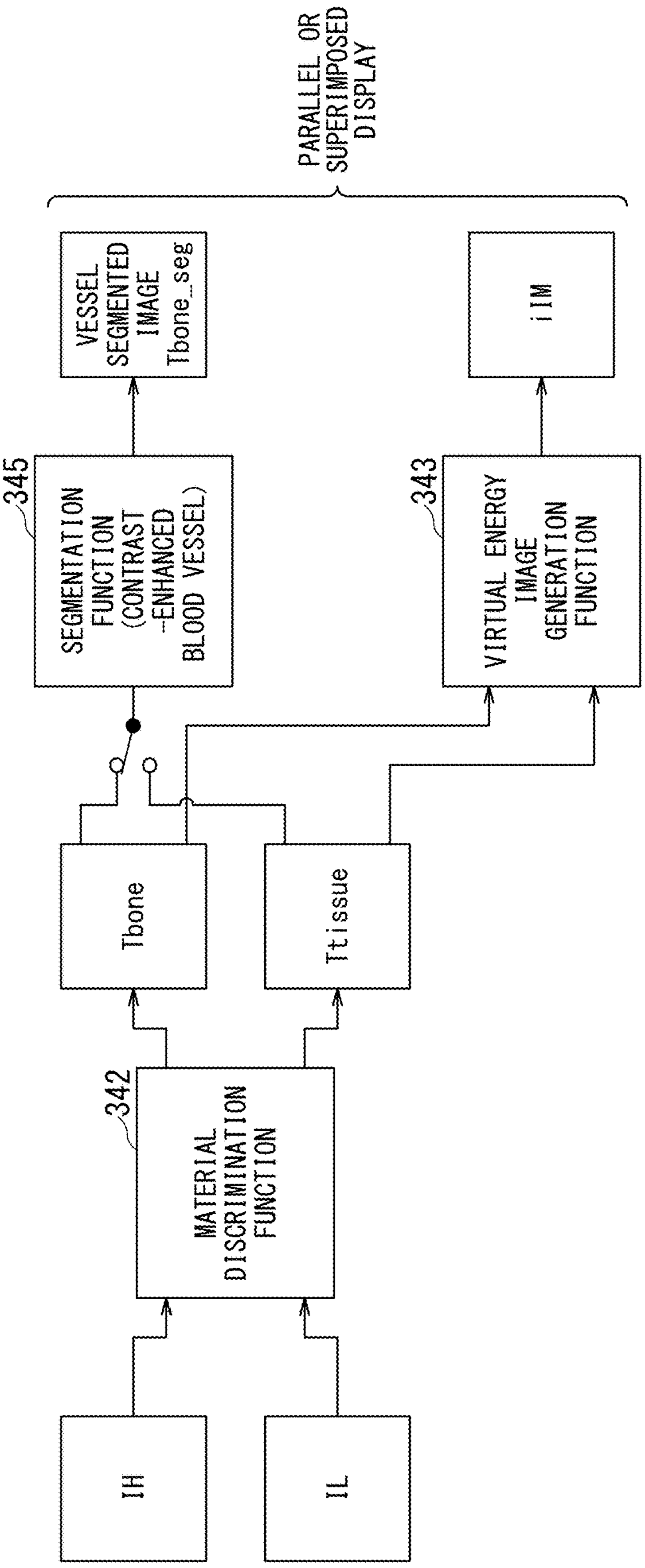
FIG. 18 is a diagram showing an example of a data flow when generating a bone thickness image Tbone_seg by segmenting contrast-enhanced blood vessels based on the bone thickness image Tbone.

FIG. 18 is a diagram illustrating one example of a data flow when the vessel segmented image Tbone_seg (bone thickness image obtained by segmenting the contrast-enhanced blood vessel on the basis of the bone thickness image Tbone) is generated.

When the high energy captured image IH and the low energy captured image IL are acquired in Step S12 and Step S13, the material discrimination function 342 then generates the bone thickness image Tbone and the soft-tissue thickness image Ttissue by the material discrimination processing based on the high energy captured image IH and the low energy captured image IL in Step S21 same as Step S4 in FIG. 2 (see the left side of FIG. 17A and FIG. 18).

In the procedures illustrated in FIGS. 16 to 18, the material discrimination function 342 calculates, in the material discrimination processing, the bone thickness $d_{bone}$ (including the bone, the contrast-enhanced blood vessel, and the like) and the soft tissue thickness dsoft, which satisfy simultaneous equations of equations (1) and (2), for each pixel of the high energy captured image IH and the low energy captured image IL same as the procedures illustrated in FIGS. 2 to 4.

The material discrimination function 342 generates the bone thickness image Tbone (see the left side of FIG. 17A) by assigning each pixel a luminance value in accordance with the bone thickness donne and the like obtained for each pixel to each pixel, and generates the soft-tissue thickness image Ttissue such that each pixel has a luminance value in accordance with the soft tissue thickness dsoft obtained for each pixel.

Next, in Step S22, the segmentation function 345 segments the target in an image out of a first material discrimination image and a second material discrimination image including the target.

As the segmentation method, various methods such as an active contour method (snakes method), a Level Set method, and a semantic segmentation method using a trained model constructed by machine learning have hitherto been known, and it is possible to use any of the above. The case where the semantic segmentation is used is described later with reference to FIGS. 19 and 20.

In the first material discrimination image or the second material discrimination image, the contrast between the materials is stronger than that in the X-ray image. Therefore, a more accurate segmentation can be expected by segmenting the first material discrimination image or the second material discrimination image than by segmenting the X-ray image.

For example, when the target is a soft tissue, at least the soft tissue is segmented in the soft-tissue thickness image Ttissue.

When the target is a contrast-enhanced blood vessel, the segmentation function 345 generates the blood-vessel segmentation-completed image Tbone_seg including the segmented contrast-enhanced blood vessels VEs by segmenting at least the contrast-enhanced blood vessel VE in the bone thickness image Tbone (see the right side of FIG. 17A). This is because the X-ray absorption coefficient of the contrast agent for performing contrast imaging of the blood vessel is close to that of the bone, and hence the contrast-enhanced blood vessel VE (third material) is visualized in the bone thickness image Tbone together with the bone (see the left side of FIG. 17A).

Next, in Step S23, the virtual energy image generation function 343 generates the normal energy virtual image iIM by performing virtual projection processing using spectrum of a virtual X-ray energy for each pixel of the bone thickness image Tbone and the soft-tissue thickness image Ttissue.

Specifically, the virtual energy image generation function 343 generates the normal energy virtual image iIM by substituting the bone thickness and the like and the soft tissue thickness $d_{soft}$ obtained in Step S21 into equation (5) and simulating projection for each pixel with use of the spectrum N(middle) (E) of a virtual third X-ray energy (for example, normal energy suitable for normal clinical use) same as Step S5 in FIG. 2 (see the left side of FIG. 17B and FIG. 18).

Next, in Step S24, the display control function 344 displays a segmentation result on the display 25 or the display 31. At this time, it is preferred that the display control function 344 display the segmentation result on the display 25 or the display 31 in parallel with or being superimposed on the normal energy virtual image iIM (see the right side of FIG. 17B).

As described above, the bone thickness image Tbone and the soft-tissue thickness image Ttissue are images indicating the thickness distribution of materials, and hence the contrast in the bone thickness image Tbone and the soft-tissue thickness image Ttissue is different from that in a normal X-ray image. Thus, such difference can be unfamiliar to the user, and make intuitive observation difficult. Therefore, when the segmentation result is superimposed on the normal energy virtual image iIM, the user can observe an image having a familiar contrast and a diagnosis can be more accurate as compared to a case where the segmentation result is superimposed on the bone thickness image Tbone.

The segmentation result superimposed on the normal energy virtual image iIM may be the blood-vessel segmentation-completed image Tbone_seg itself or may be only the segmented contrast-enhanced blood vessels VEs. In the right side of FIG. 17B and FIG. 18, one example of a case where the segmented contrast-enhanced blood vessels VEs is superimposed on the normal energy virtual image iIM is shown. The segmented contrast-enhanced blood vessels VEs may be superimposed on the high energy captured image IH or the low energy captured image IL.

By the procedures above, the target can be segmented from the material discrimination image such as the bone thickness image Tbone or the soft-tissue thickness image Ttissue. By the procedures above, an image suitable for normal clinical use can be virtually generated, and the segmentation result can be displayed on the image in a superimposed manner by simply performing X-ray imaging using extreme X-ray energies in the spectral imaging technology without additional X-ray imaging for generating an image suitable for normal clinical use, thereby preventing increased exposure dose of the object.

Next, a method of segmenting the target from the material discrimination image by semantic segmentation using a trained model is described.

The segmentation function 345 may detect the target from the material discrimination image by performing semantic segmentation with use of a trained model constructed by machine learning. In this case, deep learning using a multilayered neural network such as a CNN and a convolutional deep belief network may be adopted for the machine learning. An example of a case where the segmentation function 345 uses a trained model constructed by deep learning is described below.

Figure 19:
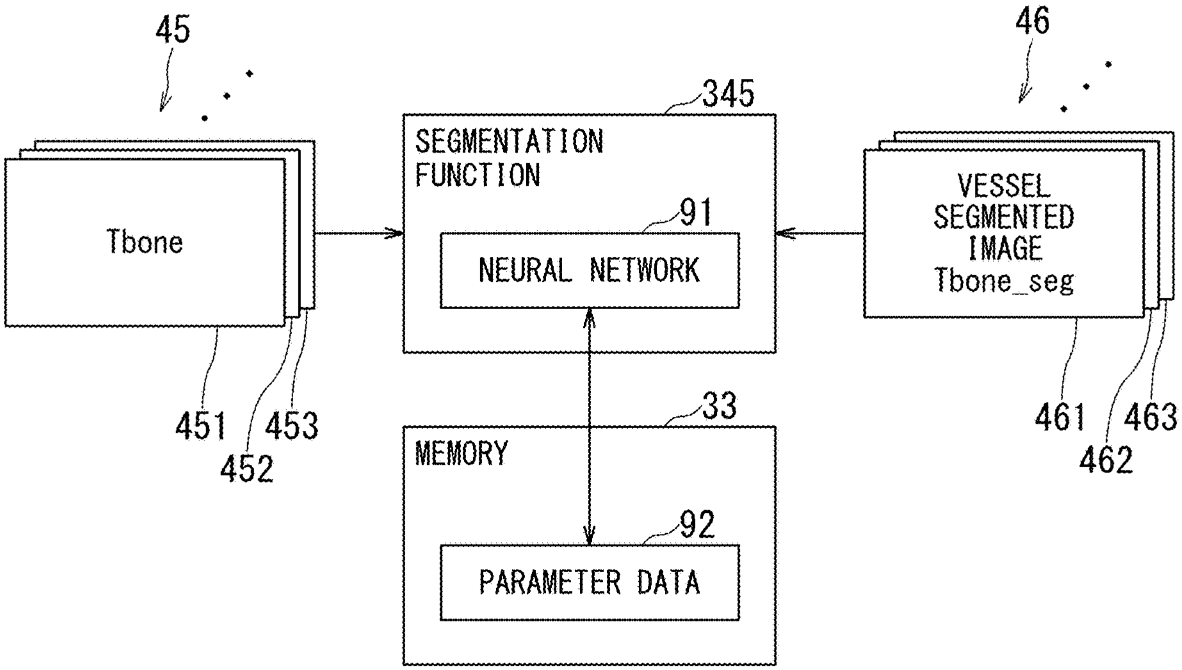
FIG. 19 is an explanatory diagram showing an example of a data flow during learning of the segmentation function according to the fourth embodiment.

FIG. 19 is an explanatory diagram illustrating one example of a data flow at the time of learning of the segmentation function 345 according to the first embodiment. The segmentation function 345 sequentially updates the parameter data 92 by performing deep learning with use of a large number of training datasets.

As the trained model, a different model is constructed and used for each target. A trained model used in a case where the target is the contrast-enhanced blood vessel is described below.

Each training dataset of the large number of training datasets consists of a set of the training data 45 and the teaching data 46. The training data 45 is bone thickness images Tbone 451, 452, 453, . . . including the contrast-enhanced blood vessel VE. The teaching data 46 is blood-vessel segmentation-completed images Tbone_seg 461, 462, 463, . . . corresponding to the bone thickness images Tbone 451, 452, 453, . . . .

The blood-vessel segmentation-completed images Tbone_seg 461, 462, 463, . . . are obtained by manually segmenting the bone thickness images Tbone 451, 452, 453, . . . , for example. When the target is the contrast-enhanced blood vessel, the segmentation is performed so as to classify the blood-vessel segmentation-completed image Tbone_seg into a region of the contrast-enhanced blood vessel and other regions, for example.

Each time a training data set is given, the segmentation function 345 performs so-called learning, that is to update the parameter data 92 such that a result obtained by processing the training data 45 by the neural network 91 approaches the teaching data 46. The parameter data 92 after the learning is hereinafter particularly referred to as trained parameter data 92*t*. The neural network 91 and the trained parameter data 92*t* configure the trained model 90.

Figure 20:
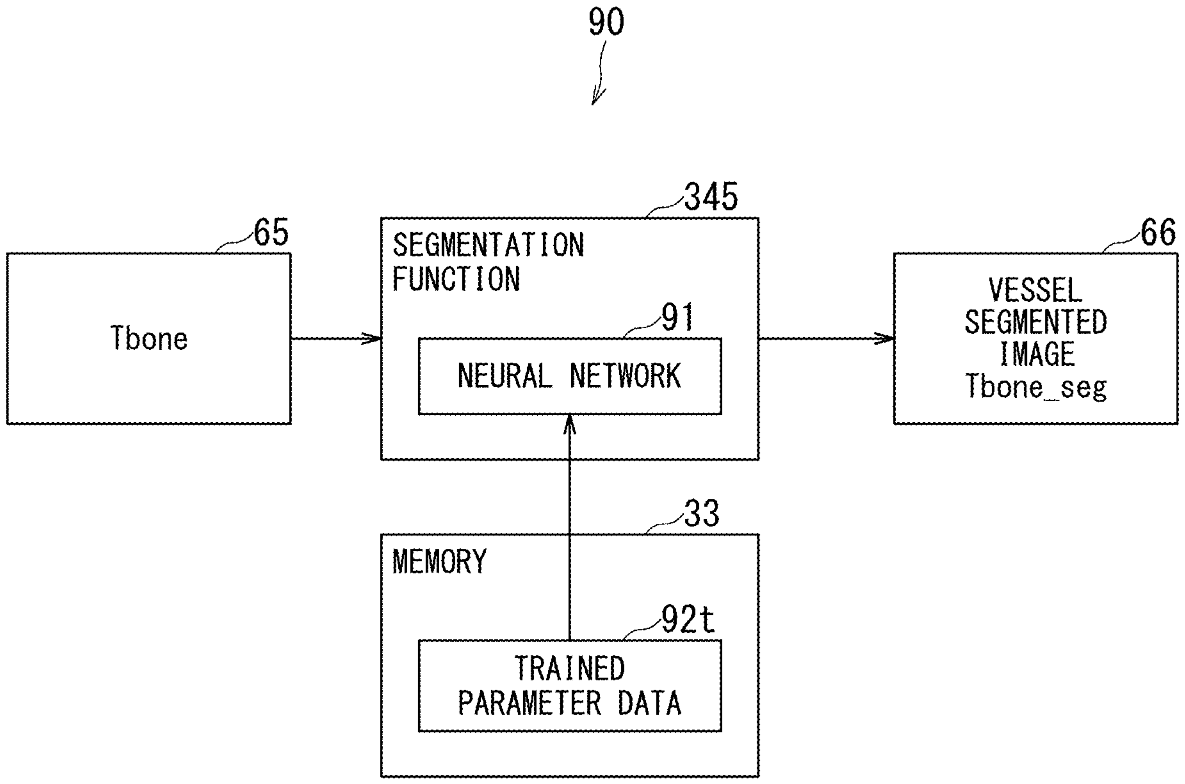
FIG. 20 is an explanatory diagram showing an example of a data flow during operation of the segmentation function according to the fourth embodiment.

FIG. 20 is an explanatory diagram illustrating one example of a data flow at the time of operation of the segmentation function 345 according to the fourth embodiment. At the time of operation, a bone thickness image Tbone 65 including the contrast-enhanced blood vessel VE is input to the segmentation function 345, and the segmentation function 345 generates a blood-vessel segmentation-completed image Tbone_seg 66 with use of the trained model 90.

The trained model 90 is configured by the neural network 91 and the trained parameter data 92*t*. As a learning method and a method of constructing a trained model of this type, various methods disclosed in published literatures have been known (Bishop, Christopher. M. (2006). *Pattern recognition and machine learning*, pp. 225-290: Springer, for example). The neural network 91 is stored in the memory 33 in a form of a program. The trained parameter data 92*t* may be stored in the memory 33 or may be stored in a storage medium connected to the processing circuitry 34 over a network.

When the trained model 90 (the neural network 91 and the trained parameter data 92*t*) is stored in the memory 33, the segmentation function 345 realized by the processor of the processing circuitry 34 can generate the blood-vessel segmentation-completed image Tbone_seg 66 from the bone thickness image Tbone 65 including the contrast-enhanced blood vessel VE by reading out the trained model 90 from the memory 33 and executing the trained model 90.

The trained model 90 may be constructed by an integrated circuit such as an application specific integrated circuit (ASIC) and a field programmable gate array (FPGA).

Fifth Embodiment

The X-ray diagnostic apparatus 10, a medical image processing apparatus, and a medical image processing method described in the fifth embodiment is different from the X-ray diagnostic apparatus 10, the medical image processing apparatus, and the medical image processing method described in the fourth embodiment in that the blood-vessel segmentation-completed image Tbone_seg is generated on the basis of the high energy captured image IH and the low energy captured image IL and not from the bone thickness image Tbone.

Figure 21:
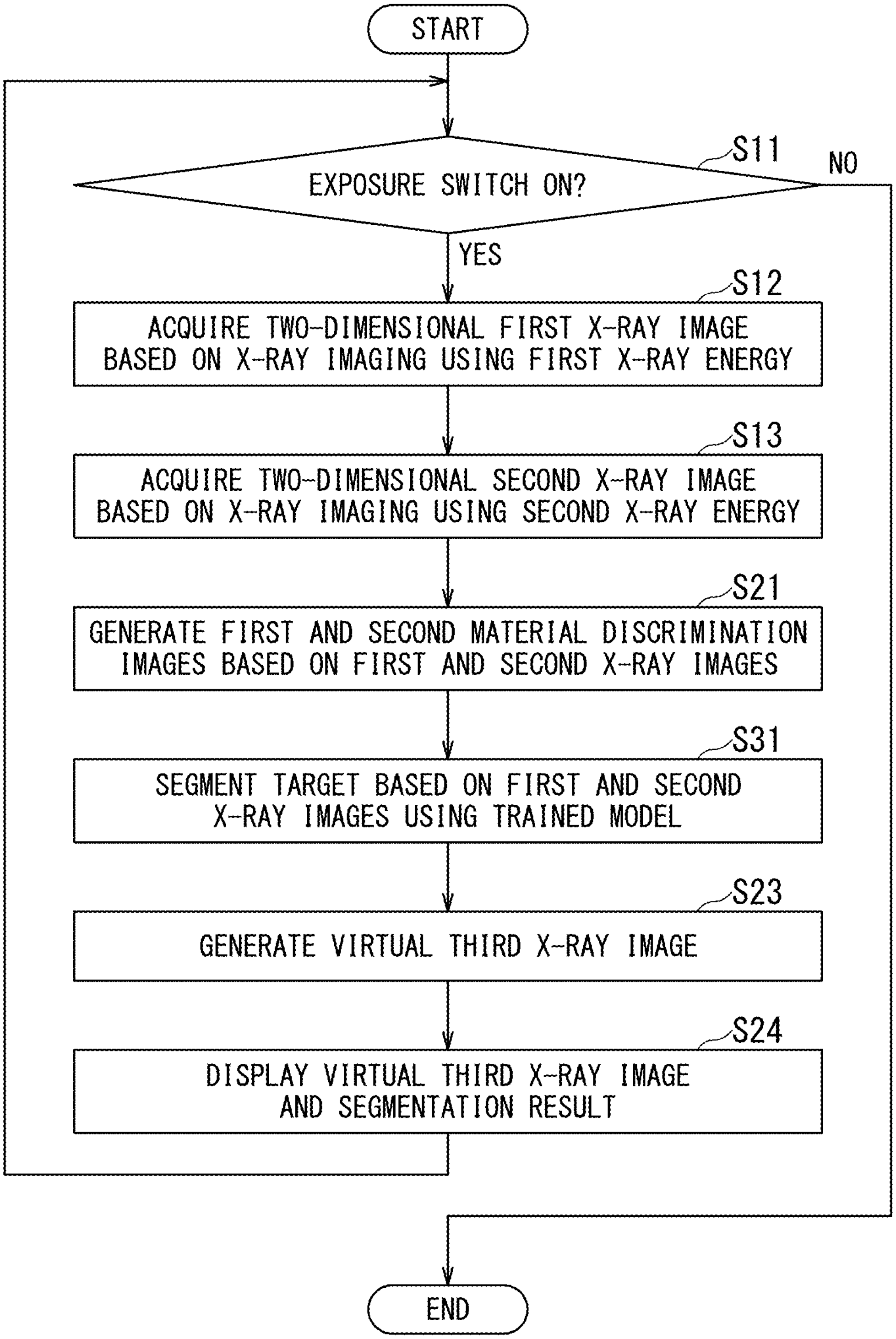
FIG. 21 is a flowchart showing an example of a segmentation procedure according to the fifth embodiment.

FIG. 21 is a flowchart illustrating one example of segmentation procedures according to the fourth embodiment. In FIG. 21, numerals attached to S indicate steps of the flowchart. Steps equivalent to those in FIG. 15 and FIG. 16 are denoted by the same numerals, and overlapping description thereof is omitted.

Figure 22:
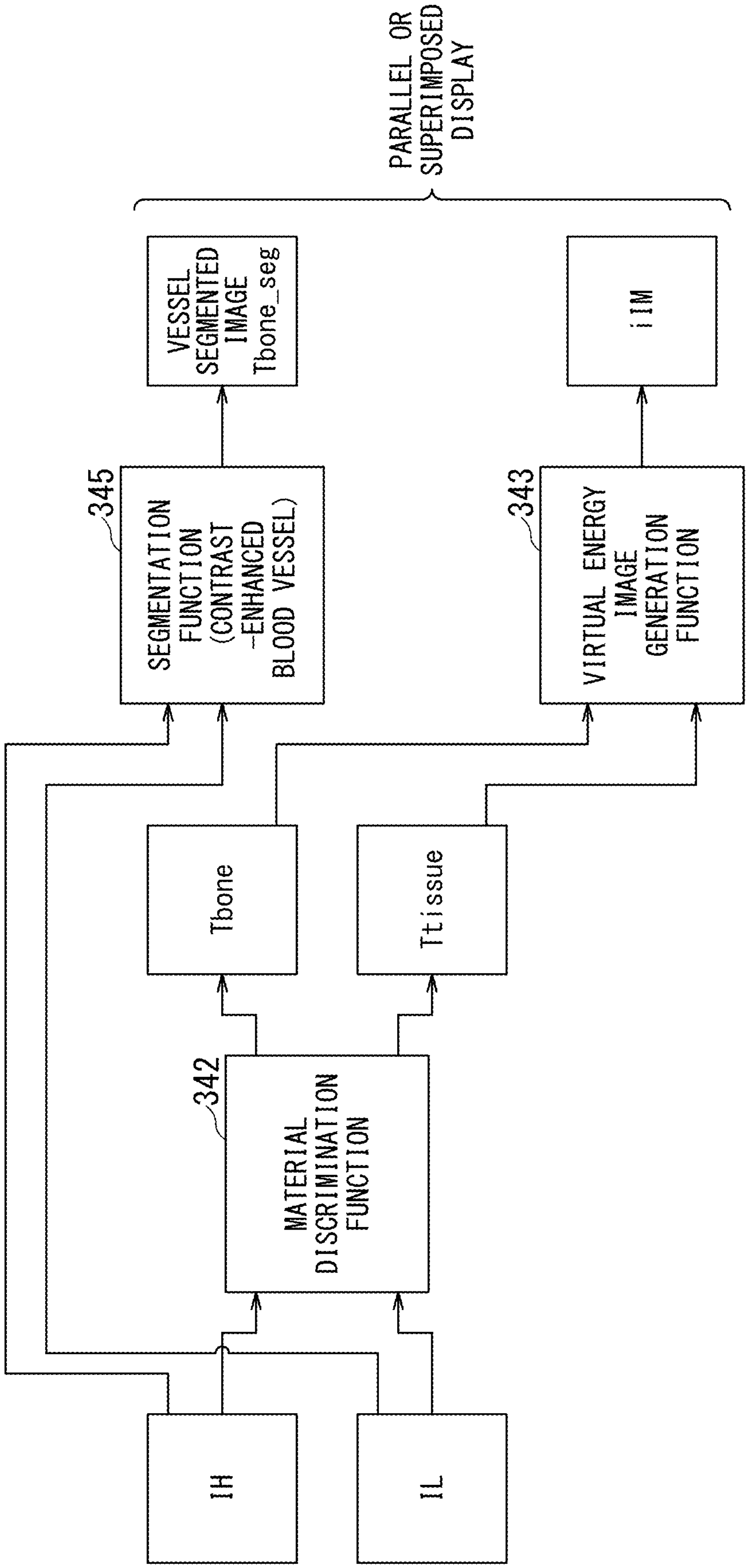
FIG. 22 is a diagram showing an example of a data flow when generating a blood vessel segmented image Tbone_seg based on a high energy captured image IH and a low energy captured image IL.

FIG. 22 is a diagram illustrating one example of a data flow when the blood-vessel segmentation-completed image Tbone_seg is generated on the basis of the high energy captured image IH and the low energy captured image IL.

When the bone thickness image Tbone and the soft-tissue thickness image Ttissue are generated in Step S21, the segmentation function 345 segments a target on the basis of the high energy captured image IH including the target and the low energy captured image IL including the target in Step S31 (see FIG. 22).

Figure 23:
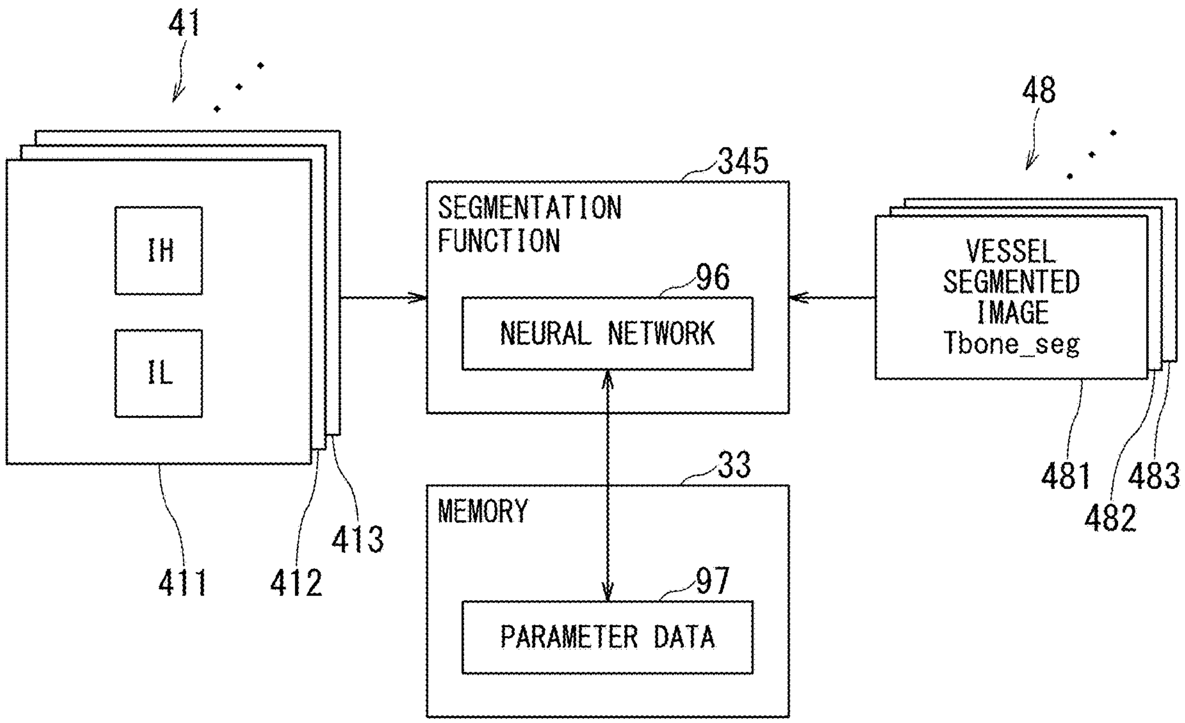
FIG. 23 is an explanatory diagram showing an example of a data flow during learning of the segmentation function according to the fifth embodiment.

FIG. 23 is an explanatory diagram illustrating one example of a data flow at the time of learning of the segmentation function 345 according to the fifth embodiment.

A training dataset of the segmentation function 345 according to the fifth embodiment consists of the training data 41 and the teaching data 48. The training data 41 is the datasets 411, 412, 413, . . . of the high energy captured image IH and the low energy captured image IL. The training data 48 is blood-vessel segmentation-completed images Tbone_seg 481, 482, 483, . . . . The training data 48 may be an image obtained by manually segmenting the contrast-enhanced blood vessel in at least one of the high energy captured image IH and the low energy captured image IL, for example, or may be an image obtained by manually segmenting the contrast-enhanced blood vessel in the bone thickness image Tbone generated on the basis of the high energy captured image IH and the low energy captured image IL, for example, same as the training data 46 of the segmentation function 345 according to the fourth embodiment.

Each time a training dataset is given, the segmentation function 345 acquires the trained parameter data 97*t* by updating the parameter data 97 such that a result obtained by processing the training data 41 by the neural network 96 approaches the training data 48. The neural network 96 and the trained parameter data 97*t* configure the trained model 95.

Figure 24:
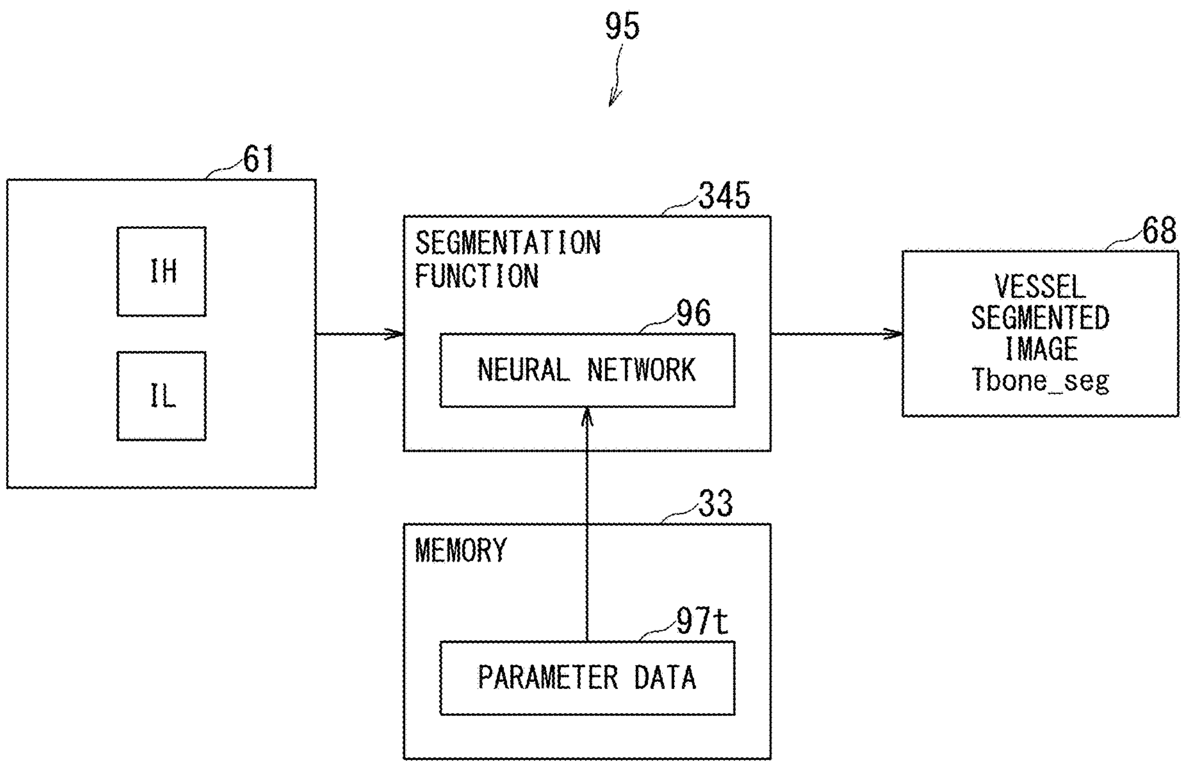
FIG. 24 is an explanatory diagram showing an example of a data flow during operation of the segmentation function according to the fifth embodiment.

FIG. 24 is an explanatory diagram illustrating one example of a data flow at the time of operation of the segmentation function 345 according to the fifth embodiment.

In the fifth embodiment, at the time of execution, only the set 61 of the high energy captured image IH and the low energy captured image IL needs to be input to the segmentation function 345, and the segmentation function 345 only needs to generate the blood-vessel segmentation-completed image Tbone_seg68 with use of the trained model 95.

In the segmentation based on one X-ray image corresponding to one X-ray energy, there are cases where the target cannot be distinguished because a background is dark and dense or because the contrast of the target is poor. Even in those cases, the segmentation function 345 of the X-ray diagnostic apparatus 10 according to the second embodiment can segment the target on the basis of the plurality of X-ray images respectively corresponding to the plurality of X-ray energies, and hence can segment the target at a high accuracy.

As to the first to third embodiments, the virtual energy image generation function 343 may generate the normal energy virtual image iIM from the high energy captured image IH and the low energy captured image IL with use of the trained model constructed by machine learning. In this case, Step S21 in FIG. 21 may be omitted.

According to at least one embodiment described above, an image suitable for normal clinical use can be acquired on the basis of X-ray imaging obtained by the spectral imaging technology while increasing the accuracy of the processing of the spectral imaging technology.

In the above-described embodiments, the term "processor" means, for example, a circuit such as a special-purpose or general-purpose CPU (Central Processing Unit), a special-purpose or general-purpose GPU (Graphics Processing Unit), an ASIC, and a programmable logic device including: an SPLD (Simple Programmable Logic Device); a CPLD (Complex Programmable Logic Device); and an FPGA. When the processor is, for example, a CPU, the processor implements various functions by reading out programs stored in a memory and executing the programs.

Additionally, when the processor is, for example, an ASIC, instead of storing the programs in the memory, the functions corresponding to the respective programs are directly incorporated as a logic circuit in the circuit of the processor. In this case, the processor implements various functions by hardware processing in which the programs incorporated in the circuit are read out and executed. Further, the processor can also implement various functions by executing software processing and hardware processing in combination.

Although a description has been given of the case where a single processor of the processing circuitry implements each function in the above-described embodiments, the processing circuitry may be configured by combining a plurality of independent processors which implement the respective functions. When a plurality of processors is provided, the memory for storing the programs may be individually provided for each processor or one memory may collectively store the programs corresponding to the functions of all the processors.

While certain embodiments have been described, these embodiments have been presented by way of example only, and are not intended to limit the scope of the inventions. These embodiments can be implemented in various other aspects, and various omissions, substitutions, changes, and combinations of embodiments can be made without departing from the spirit of the invention. These embodiments and modifications thereof are included in the scope of the invention and the gist thereof, and are also included in the invention described in the claims and the equivalent scope thereof.

(aspect 1) For instance, an X-ray diagnostic apparatus according to an embodiment includes an image acquisition unit and a virtual image generation unit. The image acquisition unit acquires a two-dimensional first X-ray image based on X-ray imaging using a first X-ray energy, and an X-ray image using a second X-ray energy different from the first X-ray energy. The virtual image generation unit generates a two-dimensional virtual third X-ray image that simulates an image using a third X-ray energy different from the first X-ray energy and the second X-ray energy, based on the first X-ray image and the second X-ray image.

The X-ray diagnostic apparatus may further include a discrimination unit configured to generate a first material discrimination image and a second material discrimination image based on the first X-ray image and the second X-ray image. Wherein, the virtual image generation unit may generate the virtual third X-ray image, by performing virtual projection processing using a spectrum corresponding to the third continuous X-ray spectrum for each pixel of the first material discrimination image and the second material discrimination image.

The virtual image generation unit may simulate a spectral projection corresponding to the third continuous X-ray spectrum, by virtually adjusting at least one of a tube voltage and a beam filter.

The X-ray diagnostic apparatus may further include an input interface that accepts an exposure instruction operation from an operator, wherein, the image acquisition unit and the virtual image generation unit may sequentially repeat combination of acquisition of the first X-ray image, acquisition of the second X-ray image, and generation of the virtual third X-ray image, on condition that the exposure instruction is continued.

The X-ray diagnostic apparatus may further include a display and a display control unit, wherein the display control unit may be configured to cause the display to display the virtual third X-ray image in parallel with at least one of the first material discrimination image and the second material discrimination image, display the virtual third X-ray image superimposed on at least one of the first material discrimination image and the second material discrimination image, or display the virtual third X-ray image superimposed on an image based on at least one of the first material discrimination image and the second material discrimination image.

The discrimination unit may determine thicknesses of the first material and the second material based on the first X-ray image and the second X-ray image, and generate the first material discrimination image and the second material discrimination image such that pixels of the first material discrimination image and the second material discrimination image respectively have luminance values corresponding to the thicknesses of the first material and the second material.

The virtual image generation unit may generate a virtual first material discrimination image and a virtual second material discrimination image simulating an X-ray imaging of the first material and the second material using the third continuous X-ray spectrum, based on thicknesses of the first material and the second material, and the display control unit may cause the display to display the virtual third X-ray image in parallel with at least one of the virtual first material discrimination image and the virtual second material discrimination image, display the virtual third X-ray image superimposed on at least one of the virtual first material discrimination image and the virtual second material discrimination image, or display the virtual third X-ray image superimposed on an image based on the at least one of the virtual first material discrimination image and the virtual second material discrimination image.

The virtual image generation unit may generate the virtual third X-ray image, by inputting the first X-ray image and the second X-ray image to a trained model that is configured to generate the virtual third X-ray image based on the first X-ray image and the second X-ray image.

The image acquisition unit further may acquire a two-dimensional actual third X-ray image based on actual X-ray imaging using the third continuous X-ray spectrum, and the virtual image generation unit may generate a corrected virtual third X-ray image based on the actual third X-ray image and the virtual third X-ray image.

The actual third X-ray image may be acquired by performing an actual X-ray imaging using the third continuous X-ray spectrum at a lower dose than normal X-ray imaging. The dose in actual X-ray imaging using the third continuous X-ray spectrum may be smaller than the dose in the case of acquiring an X-ray image having the same signal to noise (SN) ratio as the corrected virtual third X-ray image by X-ray imaging.

The virtual image generation unit may generate the corrected virtual third X-ray image, by inputting the first X-ray image, the second X-ray image, and the actual third X-ray image to a trained model that is configured to generate the corrected virtual third X-ray image based on the first X-ray image, the second X-ray image, and the actual third X-ray image.

The trained model may be constructed by using training datasets including training data and teaching data, wherein the training data includes the first X-ray image, the second X-ray image, and a coarse third X-ray image generated by adding noise to a fine third X-ray image obtained by performing actual X-ray imaging using the third continuous X-ray spectrum at a dose equal to or greater than that of a normal X-ray imaging, and the teaching data includes the fine third X-ray image.

The X-ray diagnostic apparatus may further include a discrimination unit configured to generate a first material discrimination image and a second material discrimination image based on the first X-ray image and the second X-ray image, wherein, the discrimination unit may compare the actual third X-ray image and the virtual third X-ray image to generate a contrast-enhanced blood vessel discrimination image in which contrast-enhanced blood vessels are extracted.

(aspect 2) A medical image processing apparatus according to one embodiment include: an image acquisition unit configured to acquire a two-dimensional first X-ray image based on X-ray imaging using a first continuous X-ray spectrum, and acquire a two-dimensional second X-ray image based on X-ray imaging using a second continuous X-ray spectrum different from the first continuous X-ray spectrum; and a virtual image generation unit configured to generate a two-dimensional virtual third X-ray image that simulates an X-ray image using a third continuous X-ray spectrum different from the first continuous X-ray spectrum and the second continuous X-ray spectrum, based on the first X-ray image and the second X-ray image.

(aspect 3) A medical image processing method according to one embodiment includes: acquiring a two-dimensional first X-ray image based on X-ray imaging using a first continuous X-ray spectrum, and acquire a two-dimensional second X-ray image based on X-ray imaging using a second continuous X-ray spectrum different from the first continuous X-ray spectrum; and generating a two-dimensional virtual third X-ray image that simulates an X-ray image using a third continuous X-ray spectrum different from the first continuous X-ray spectrum and the second continuous X-ray spectrum, based on the first X-ray image and the second X-ray image.

(aspect 4) An X-ray diagnostic apparatus according to one embodiment includes a segmentation unit and an image acquisition unit. Wherein, the image acquisition unit acquires the first two-dimensional X-ray image including a target based on X-ray imaging using the first continuous X-ray spectrum, and acquires the second two-dimensional X-ray image including a target based on X-ray imaging using the second continuous X-ray spectrum, and the segmentation unit segments the target based on the first X-ray image and the second X-ray image.

An X-ray diagnostic apparatus may further include a virtual image generation unit configured to generate a two-dimensional virtual third X-ray image that simulates an X-ray image using a third continuous X-ray spectrum different from the first continuous X-ray spectrum and the second continuous X-ray spectrum, based on the first X-ray image and the second X-ray image, and a display control unit configured to cause a display to display the segmented image of the target superimposed on the virtual third X-ray image, or cause the display to display it in parallel with the virtual third X-ray image.

The X-ray diagnostic apparatus may further include a discrimination unit configured to generate a first material discrimination image and a second material discrimination image based on the first X-ray image and the second X-ray image, wherein, the virtual image generation unit may generate the virtual third X-ray image, by performing virtual projection processing using a spectrum corresponding to the third continuous X-ray spectrum for each pixel of the first material discrimination image and the second material discrimination image.

The discrimination unit may determine thicknesses of the first material and the second material based on the first X-ray image and the second X-ray image, and generate the first material discrimination image and the second material discrimination image such that pixels of the first material discrimination image and the second material discrimination image respectively have luminance values corresponding to the thicknesses of the first material and the second material.

The target may be a first material or a third material depicted in the first material discrimination image, or a second material depicted in the second material discrimination image. In this case, the segmentation unit may generate an image in which the first material or the third material is segmented, by inputs the first material discrimination image to a trained model that is configured to generate an image in which the first material or the third material is segmented, based on the first material discrimination image.

Alternatively, the segmentation unit may generate an image in which the second material is segmented, by inputting the second material discrimination image to a trained model that is configured to generate an image in which the second material is segmented based on the second material discrimination image.

The segmentation unit may generate a segmented image of the target, by inputting the first X-ray image and the second X-ray image to a trained model that is configured to generate an image in which the target is segmented based on the first X-ray image and the second X-ray image.

The virtual image generation unit may generate the virtual third X-ray image, by inputting the first X-ray image and the second X-ray image to a trained model that is configured to generate the virtual third X-ray image based on the first X-ray image and the second X-ray image.

The X-ray diagnostic apparatus may further include a display control unit that causes the display to display the image of the segmented target superimposed on the first X-ray image or the second X-ray image.

(aspect 5) A medical image processing apparatus according to one embodiment includes an image acquisition unit and a segmentation unit. The image acquisition unit acquires a two-dimensional first X-ray image including the target based on X-ray imaging using the first continuous X-ray spectrum, and acquires a two-dimensional second x-ray image including the target based on x-ray imaging using the second continuous x-ray spectrum different from the first continuous X-ray spectrum. The segmentation unit segments the target based on the first X-ray image and the second X-ray image.

(aspect 6) A medical image processing method according to one embodiment includes: acquiring a two-dimensional first X-ray image including the target based on X-ray imaging using the first continuous X-ray spectrum, acquiring a two-dimensional second x-ray image including the target based on x-ray imaging using the second continuous x-ray spectrum different from the first continuous X-ray spectrum, and segmenting the target based on the first X-ray image and the second X-ray image.

The first X-ray image and the second X-ray image may be X-ray fluoroscopic images. The first X-ray image and the second X-ray image may be X-ray radiographic images.

The first material and second material may be a bone and a soft tissue, respectively. In this case, the first material discrimination image is a bone thickness image Tbone obtained by discriminating bones by material discrimination processing based on X-ray images, and the second material discrimination image is a soft tissue thickness image Ttissue obtained by discriminating the soft tissue by material discrimination processing based on the X-ray images.

The first continuous X-ray spectrum may correspond to a high tube voltage, the second continuous X-ray spectrum to a low tube voltage, and the third continuous X-ray spectrum to an intermediate tube voltage between the high and low tube voltages. For example, the first continuous X-ray spectrum may correspond to a tube voltage of 120-160 kV, the second continuous X-ray spectrum to the tube voltage of 40-60 kV, and the third continuous X-ray spectrum to the tube voltage of 70-90 kV.

The invention claimed is:

1. An X-ray diagnostic apparatus, comprising:

processing circuitry configured to:

acquire a two-dimensional first X-ray image obtained from X-ray imaging using a first continuous X-ray spectrum, and acquire a two-dimensional second X-ray image obtained from X-ray imaging using a second continuous X-ray spectrum different from the first continuous X-ray spectrum;

generate a two-dimensional virtual third X-ray image that simulates an X-ray image using a third continuous X-ray spectrum different from the first continuous X-ray spectrum and the second continuous X-ray spectrum, based on the first X-ray image and the second X-ray image, wherein the first continuous X-ray spectrum corresponds to a high tube voltage, the second continuous X-ray spectrum corresponds to a low tube voltage, and the third continuous X-ray spectrum corresponds to an intermediate tube voltage between the high and low tube voltages;

display the generated virtual third X-ray image;

acquire a two-dimensional actual third X-ray image based on X-ray imaging using the third continuous X-ray spectrum; and generate a corrected virtual third X-ray image based on the actual third X-ray image and the virtual third X-ray image.

2. The X-ray diagnostic apparatus according to claim 1, wherein the processing circuitry is further configured to:

determine respective thicknesses of a first material and a second material based on the first X-ray image and the second X-ray image; and generate the virtual third X-ray image, by performing virtual projection processing using a spectrum corresponding to the third continuous X-ray spectrum, based on the determined thicknesses of the first material and the second material.

3. The X-ray diagnostic apparatus according to claim 1, wherein the processing circuitry is further configured to simulate a spectral projection corresponding to the third continuous X-ray spectrum, by virtually adjusting at least one of a tube voltage and a beam filter.

4. The X-ray diagnostic apparatus according to claim 2, wherein the processing circuitry is further configured to simulate a spectral projection corresponding to the third continuous X-ray spectrum, by virtually adjusting at least one of a tube voltage and a beam filter.

5. The X-ray diagnostic apparatus according to claim 2, further comprising an input interface that is configured to accept an exposure instruction operation from an operator, wherein the processing circuitry is further configured to sequentially repeat a combination of acquisition of the first X-ray image, acquisition of the second X-ray image, and generation of the virtual third X-ray image, on condition that the exposure instruction is continued.

6. The X-ray diagnostic apparatus according to claim 2, wherein the processing circuitry is further configured to:

generate a first material discrimination image and a second material discrimination image based on the first X-ray image and the second X-ray image; and cause a display to display the virtual third X-ray image in parallel with at least one of the first material discrimination image and the second material discrimination image, display the virtual third X-ray image superimposed on at least one of the first material discrimination image and the second material discrimination image, or display the virtual third X-ray image superimposed on an image based on at least one of the first material discrimination image and the second material discrimination image.

7. The X-ray diagnostic apparatus according to claim 6, wherein the processing circuitry is further configured to generate the first material discrimination image and the second material discrimination image such that pixels of the first material discrimination image and the second material discrimination image respectively have luminance values corresponding to the thicknesses of the first material and the second material.

8. The X-ray diagnostic apparatus according to claim 1, wherein the processing circuitry is further configured to generate the virtual third X-ray image, by inputting the first X-ray image and the second X-ray image to a trained model that is configured to generate the virtual third X-ray image based on the first X-ray image and the second X-ray image.

9. The X-ray diagnostic apparatus according to claim 1, wherein the processing circuitry is further configured to acquire the actual third X-ray image by performing an X-ray imaging using the third continuous X-ray spectrum at a lower dose than normal X-ray imaging.

10. The X-ray diagnostic apparatus according to claim 1, wherein the processing circuitry is further configured such that a dose in the X-ray imaging using the third continuous X-ray spectrum is smaller than a dose in acquiring an X-ray image having a same signal to noise "SN" ratio as the corrected virtual third X-ray image by X-ray imaging.

11. The X-ray diagnostic apparatus according to claim 1, wherein the processing circuitry is further configured to generate the corrected virtual third X-ray image by inputting the first X-ray image, the second X-ray image, and the actual third X-ray image to a trained model that is configured to generate the corrected virtual third X-ray image based on the first X-ray image, the second X-ray image, and the actual third X-ray image.

12. The X-ray diagnostic apparatus according to claim 11, wherein the trained model is constructed by using training datasets including training data and teaching data, wherein the training data includes the first X-ray image, the second X-ray image, and a coarse third X-ray image generated by adding noise to a fine third X-ray image obtained by performing actual X-ray imaging using the third continuous X-ray spectrum at a dose equal to or greater than that of a normal X-ray imaging, and the teaching data includes the fine third X-ray image.

13. The X-ray diagnostic apparatus according to claim 1, wherein the processing circuitry is further configured to:

generate a first material discrimination image and a second material discrimination image based on the first X-ray image and the second X-ray image; and compare the actual third X-ray image and the virtual third X-ray image to generate a contrast-enhanced blood vessel discrimination image in which contrast-enhanced blood vessels are extracted.

14. The X-ray diagnostic apparatus according to claim 1, wherein the processing circuitry is further configured to:

acquire the first two-dimensional X-ray image including a target based on X-ray imaging using the first continuous X-ray spectrum, and acquire the second two-dimensional X-ray image including a target based on X-ray imaging using the second continuous X-ray spectrum; and segment the target based on the first X-ray image and the second X-ray image.

15. The X-ray diagnostic apparatus according to claim 14, wherein the processing circuitry is further configured to cause a display to display the segmented image of the target superimposed on the virtual third X-ray image, or cause the display to display the segmented image in parallel with the virtual third X-ray image.

16. The X-ray diagnostic apparatus according to claim 15, wherein the processing circuitry is further configured to generate a segmented image of the target by inputting the first X-ray image and the second X-ray image to a trained model that is configured to generate an image in which the target is segmented based on the first X-ray image and the second X-ray image.

17. An X-ray diagnostic apparatus, comprising:

processing circuitry configured to:

acquire a two-dimensional first X-ray image obtained from X-ray imaging using a first continuous X-ray spectrum, and acquire a two-dimensional second X-ray image obtained from X-ray imaging using a second continuous X-ray spectrum different from the first continuous X-ray spectrum;

generate a two-dimensional virtual third X-ray image that simulates an X-ray image using a third continuous X-ray spectrum different from the first continuous X-ray spectrum and the second continuous X-ray spectrum, based on the first X-ray image and the second X-ray image, wherein the first continuous X-ray spectrum corresponds to a high tube voltage, the second continuous X-ray spectrum corresponds to a low tube voltage, and the third continuous X-ray spectrum corresponds to an intermediate tube voltage between the high and low tube voltages; and display the generated virtual third X-ray image, wherein the processing circuitry is further configured to determine respective thicknesses of a first material and a second material based on the first X-ray image and the second X-ray image;

generate the virtual third X-ray image, by performing virtual projection processing using a spectrum corresponding to the third continuous X-ray spectrum, based on the determined thicknesses of the first material and the second material;

generate a first material discrimination image and a second material discrimination image based on the first X-ray image and the second X-ray image;

cause a display to display the virtual third X-ray image in parallel with at least one of the first material discrimination image and the second material discrimination image, display the virtual third X-ray image superimposed on at least one of the first material discrimination image and the second material discrimination image, or display the virtual third X-ray image superimposed on an image based on at least one of the first material discrimination image and the second material discrimination image:

generate the first material discrimination image and the second material discrimination image such that pixels of the first material discrimination image and the second material discrimination image respectively have luminance values corresponding to the thicknesses of the first material and the second material;

generate a virtual first material discrimination image and a virtual second material discrimination image simulating an X-ray imaging of the first material and the second material using the third continuous X-ray spectrum, based on the thicknesses of the first material and the second material; and cause the display to display the virtual third X-ray image in parallel with at least one of the virtual first material discrimination image and the virtual second material discrimination image, display the virtual third X-ray image superimposed on at least one of the virtual first material discrimination image and the virtual second material discrimination image, or display the virtual third X-ray image superimposed on an image based on the at least one of the virtual first material discrimination image and the virtual second material discrimination image.

18. A medical image processing apparatus, comprising:

processing circuitry configured to:

acquire a two-dimensional first X-ray image obtained from X-ray imaging using a first continuous X-ray spectrum, and acquire a two-dimensional second X-ray image obtained from X-ray imaging using a second continuous X-ray spectrum different from the first continuous X-ray spectrum;

generate a two-dimensional virtual third X-ray image that simulates an X-ray image using a third continuous X-ray spectrum different from the first continuous X-ray spectrum and the second continuous X-ray spectrum, based on the first X-ray image and the second X-ray image, wherein the first continuous X-ray spectrum corresponds to a high tube voltage, the second continuous X-ray spectrum corresponds to a low tube voltage, and the third continuous X-ray spectrum corresponds to an intermediate tube voltage between the high and low tube voltages; and display the generated virtual third X-ray image, wherein the processing circuitry is further configured to acquire a two-dimensional actual third X-ray image based on X-ray imaging using the third continuous X-ray spectrum; and generate a corrected virtual third X-ray image based on the actual third X-ray image and the virtual third X-ray image.

19. A medical image processing method, comprising:

acquiring a two-dimensional first X-ray image obtained from X-ray imaging using a first continuous X-ray spectrum, and acquire a two-dimensional second X-ray image obtained from X-ray imaging using a second continuous X-ray spectrum different from the first continuous X-ray spectrum; and generating a two-dimensional virtual third X-ray image that simulates an X-ray image using a third continuous X-ray spectrum different from the first continuous X-ray spectrum and the second continuous X-ray spectrum, based on the first X-ray image and the second X-ray image, wherein the first continuous X-ray spectrum corresponds to a high tube voltage, the second continuous X-ray spectrum corresponds to a low tube voltage, and the third continuous X-ray spectrum corresponds to an intermediate tube voltage between the high and low tube voltages; and displaying the generated virtual third X-ray image, wherein the method further comprises acquiring a two-dimensional actual third X-ray image based on X-ray imaging using the third continuous X-ray spectrum; and generating a corrected virtual third X-ray image based on the actual third X-ray image and the virtual third X-ray image.

* * * * *